US007449179B2

(12) United States Patent
Xin et al.

(10) Patent No.: US 7,449,179 B2
(45) Date of Patent: Nov. 11, 2008

(54) VECTORS FOR CONDITIONAL GENE INACTIVATION

(75) Inventors: Hong-Bo Xin, Ithaca, NY (US); Michael Kotlikoff, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 340 days.

(21) Appl. No.: 10/416,995

(22) PCT Filed: Nov. 16, 2001

(86) PCT No.: PCT/US01/43916

§ 371 (c)(1), (2), (4) Date: Nov. 6, 2003

(87) PCT Pub. No.: WO02/40685

PCT Pub. Date: May 23, 2002

(65) Prior Publication Data

US 2004/0077089 A1   Apr. 22, 2004

Related U.S. Application Data

(60) Provisional application No. 60/249,200, filed on Nov. 16, 2000.

(51) Int. Cl.
*A01N 63/00* (2006.01)
*A01N 43/04* (2006.01)
*C12N 15/00* (2006.01)
*C12N 15/63* (2006.01)
*C12N 15/87* (2006.01)

(52) U.S. Cl. .................. 424/93.21; 435/320.1; 435/455; 435/463; 514/44; 536/23.1; 536/24.1

(58) Field of Classification Search .................. 514/44; 435/320.1, 455, 463; 424/93.21; 536/23.1, 536/24.1
See application file for complete search history.

(56) References Cited

U.S. PATENT DOCUMENTS

| 5,922,927 | A | | 7/1999 | Bujard et al. .................. 800/25 |
| 6,004,750 | A | * | 12/1999 | Frank-Kamenetskii et al. . 435/6 |
| 6,436,707 | B1 | * | 8/2002 | Zambrowicz et al. ....... 435/455 |
| 7,074,611 | B2 | | 7/2006 | Chambon et al. |

FOREIGN PATENT DOCUMENTS

| EP | 1383891 B1 | 12/2005 |
| WO | WO-99/50426 | 10/1999 |
| WO | WO-01/29208 | 4/2001 |

OTHER PUBLICATIONS

Verma et al., 1997, Nature, vol. 389, pp. 239-242.*
Eck et al., 1996, Goodman & Gilman's The Pharmacological Basis of Therapeutics, McGraw-Hill, New York, p. 77-101.*
Gorecki, 2001, Expert Opin. Emerging Drugs, 6(2): 187-198.*
Araki et al., 1997, Nucleic Acids Research, vol. 25, No. 4, p. 868-872.*
Araki et al., 1999, Cellular and Moplecular Biology, vol. 45, No. 5, pp. 737-750.*
Albert, Henrik, et al., "Site-specific integration of DNA into wild-type and mutant lox sites placed in the plant genome", *The Plant Journal*, 7 (4), (1995), 649-659.
Araki, H., et al., "Site-specific recombinase, R, encoded by yeast plasmid pSR1", *Journal of Molecular Biology*. 225(1), (May 1992),25-37.
Bruning, J. C., et al., "Konditionale Mutagenese—Knockout-mause der Zweiten Generation als Modelle Internistischer Erkrankungen", *Medizinische Klinik*, 94, (Oct. 15, 1999), 564-569.
Friedrich, G., et al., "Promoter traps in embryonic stem cells: a genetic screen to identify and mutate developmental genes in mice", *Genes & Development*. 5(9), (Sep. 1991), 1513-1523.
Golic, K. G., et al., "The FLP recombinase of yeast catalyzes site-specific recombination in the Drosophila genome", *Cell*. 59(3), (Nov. 1989), 499-509.
Kano, M., et al., "Cre-IoxP-mediated DNA flip-flop in mammalian cells leadint to alternate expression of retrovirally transduced genes", *Biochemical and Biophysical Research Communications*, 248 (3), (1998), 806-811.
Kmita, M., et al., "Targeted inversion of a polar silencer within the HoxD complex re-allocates domains of enhancer sharing", *Nature Genetics*. 26(4), (Dec. 2000), 451-454.
Lam, K. P., et al., "Rapid elimination of mature autoreactive B cells demonstrated by Cre-induced change in B cell antigen receptor specificity in vivo", *Proceedings of the National Academy of Sciences of the United States of America*. 95(22), (1998), 13171-13175.
Michael, S. K., et al., "Efficient Gene-Specific Expression of Cre Recombinase in the Mouse Embryo by Targeted Insertion of a Novel IRES-Cre Cassette into Endogenous Loci", *Mechanisms of Development*, 85, (1999), 35-47.
Senecoff, J. F., et al., "DNA recognition by the FLP recombinase of the yeast 2 mu plasmid. A mutational analysis of the FLP binding site", *Journal of Molecular Biology*. 201(2), (1988), 405-421.
Wiles, M. V., et al., "Establishment of a gene-trap sequence tag library to generate mutant mice from embryonic stem cells", *Nature Genetics*. 24(1), (2000), 13-14.
Zambrowicz, B. P., et al., "Disruption and sequence identification of 2,000 genes in mouse embryonic stem cells", *Nature*. 392(6676), (1998), 608-611.

* cited by examiner

*Primary Examiner*—Shin-Lin Chen
(74) *Attorney, Agent, or Firm*—Schwegman, Lundberg & Woessner, P.A.

(57) ABSTRACT

A method of preparing gene trapping libraries, and gene targeted cells for conditional inactivation of genes, is provided. The invention provides a vector having a mutational element cassette and a gene trap cassette, each cassette having site-specific recombination sequences.

22 Claims, 12 Drawing Sheets

I. DOUBLE SWITCH VECTOR FOR ELECTROPORATION

II. DOUBLE FLIP VECTOR FOR RETROVIRAL INFECTION

STEP 1: INSERTION OF GENOMIC DNA FRAGMENTS INTO FLIPOUT VECTOR

STEP 2: INSERTION OF VECTOR INTO INTRON BY HOMOLOGOUS RECOMBINATION

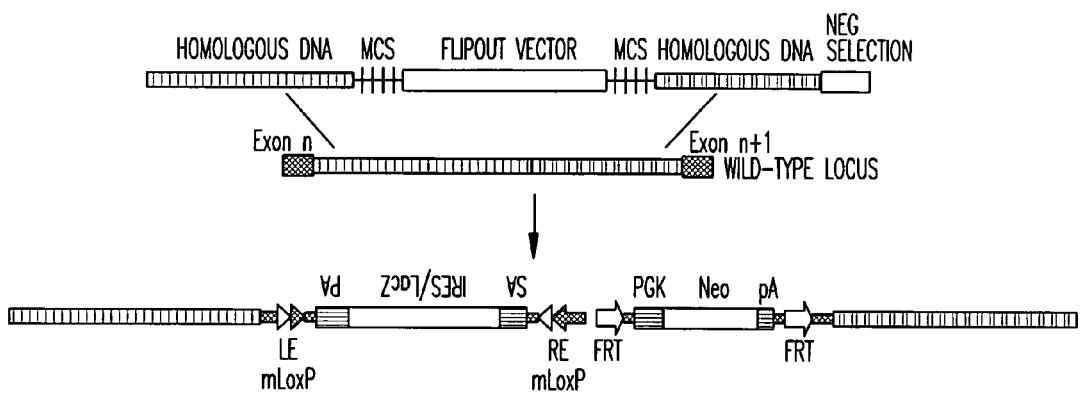

STEP 3: POSITIVE AND NEGATIVE SELECTION OF ES CELLS

STEP 4: REMOVAL OF SELECTION CASSETTE BY TRANSFECTION
WITH FRT RECOMBINASE TO GENERATE FUNCTIONAL ALLELE

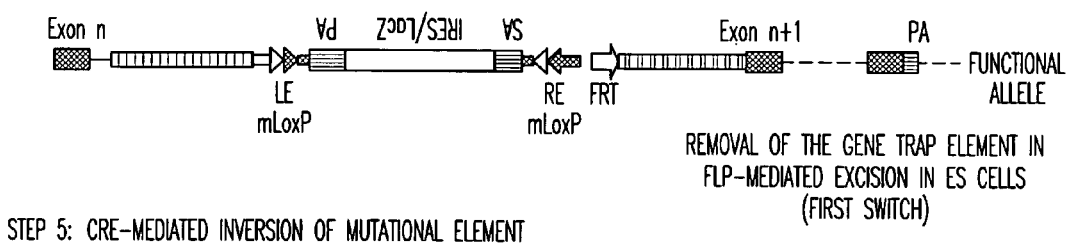

REMOVAL OF THE GENE TRAP ELEMENT IN
FLP-MEDIATED EXCISION IN ES CELLS
(FIRST SWITCH)

STEP 5: CRE-MEDIATED INVERSION OF MUTATIONAL ELEMENT
IN VIVO TO CREATE A CONDITIONAL KNOCKOUT MOUSE

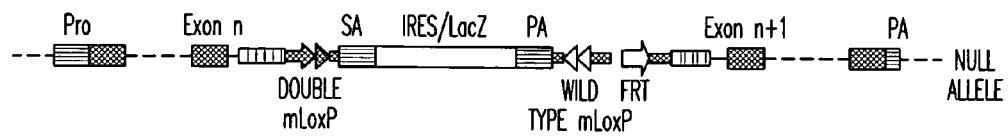

*FIG. 4B*

SEQUENCE LISTING

```
<160> NUMBER OF SEQ ID NOS: 12

<210> SEQ ID NO 1
<211> LENGTH: 21
<212> TYPE: DNA
<213> ORGANISM: Artificial Sequence
<220> FEATURE:
<223> OTHER INFORMATION: A primer

<400> SEQUENCE: 1
cgggatccag gcaaaacgtc g                                           21

<210> SEQ ID NO 2
<211> LENGTH: 21
<212> TYPE: DNA
<213> ORGANISM: Artificial Sequence
<220> FEATURE:
<223> OTHER INFORMATION: A primer

<400> SEQUENCE: 2
gctctagatg gtgatccggc c                                           21

<210> SEQ ID NO 3
<211> LENGTH: 21
<212> TYPE: DNA
<213> ORGANISM: Artificial Sequence
<220> FEATURE:
<223> OTHER INFORMATION: A primer

<400> SEQUENCE: 3
gtttcactat ccaggttacg g                                           21

<210> SEQ ID NO 4
<211> LENGTH: 21
<212> TYPE: DNA
<213> ORGANISM: Artificial Sequence
<220> FEATURE:
<223> OTHER INFORMATION: A primer
```

```
<400> SEQUENCE: 4
ccaatttact gaccgtacac c                                              21

<210> SEQ ID NO 5
<211> LENGTH: 21
<212> TYPE: DNA
<213> ORGANISM: Artificial Sequence
<220> FEATURE:
<223> OTHER INFORMATION: A primer

<400> SEQUENCE: 5
aagcttgctg tatctctaag a                                              21

<210> SEQ ID NO 6
<211> LENGTH: 21
<212> TYPE: DNA
<213> ORGANISM: Artificial Sequence
<220> FEATURE:
<223> OTHER INFORMATION: A primer

<400> SEQUENCE: 6
cgaattcact cacctagcat a                                              21

<210> SEQ ID NO 7
<211> LENGTH: 21
<212> TYPE: DNA
<213> ORGANISM: Artificial Sequence
<220> FEATURE:
<223> OTHER INFORMATION: A primer

<400> SEQUENCE: 7
ggtttagtga accgtcagat c                                              21

<210> SEQ ID NO 8
<211> LENGTH: 21
<212> TYPE: DNA
<213> ORGANISM: Artificial Sequence
<220> FEATURE:
<223> OTHER INFORMATION: A primer

<400> SEQUENCE: 8
cgaattcact cacctagcat a                                              21

<210> SEQ ID NO 9
<211> LENGTH: 34
<212> TYPE: DNA
<213> ORGANISM: Artificial Sequence
<220> FEATURE:
<223> OTHER INFORMATION: A mutant loxP sequence

<400> SEQUENCE: 9
ataacttcgt ataatgtatg ctatacgaac ggta                                34

<210> SEQ ID NO 10
<211> LENGTH: 34
<212> TYPE: DNA
<213> ORGANISM: Artificial Sequence
<220> FEATURE:
<223> OTHER INFORMATION: A mutant loxP sequence

<400> SEQUENCE: 10
ataacttcgt atagcataca ttatacgaac ggta                                34

<210> SEQ ID NO 11
<211> LENGTH: 48
```

-continued

```
<212> TYPE: DNA
<213> ORGANISM: Artificial Sequence
<220> FEATURE:
<223> OTHER INFORMATION: A mutant FRT sequence

<400> SEQUENCE: 11
gaagttccta ttccgaagtt cctattctct agaaagtata agaacttc                    48

<210> SEQ ID NO 12
<211> LENGTH: 48
<212> TYPE: DNA
<213> ORGANISM: Artificial Sequence
<220> FEATURE:
<223> OTHER INFORMATION: A mutant FRT sequence

<400> SEQUENCE: 12
gaagttccta tactttctag agaataagaa cttcggaata ggaacttc                    48
```

VECTORS FOR CONDITIONAL GENE INACTIVATION

CROSS-REFERENCE TO RELATED APPLICATIONS

This application is a U.S. National Stage application under 35 U.S.C. 371 from International Application No. PCT/US01/43916, filed 16 Nov. 2001 and published in English as WO 02/40685 A2 and published on 23 May 2002, which claimed priority under 35 U.S.C. 119(e) from U.S. Provisional Application Ser. No. 60/249,200 filed 16 Nov. 2000, which applications and publication are incorporated herein by reference.

BACKGROUND OF THE INVENTION

To make practical use of the complete sequence of the human and murine genomes, it is necessary to determine the biological function of individual genes. Selective gene inactivation (knockout) in the mouse in embryonic stem (ES) cells using gene trap vectors has emerged as a powerful experimental tool in this regard.

Most mammalian genes are divided into exons and introns. Exons are the portions of the gene that are spliced into mRNA and encode the protein product of a gene. In genomic DNA, these coding exons are divided by noncoding intron sequences. Although RNA polymerase transcribes both intron and exon sequences, the intron sequences must be removed from the transcript so that the resulting mRNA can be translated into protein. Accordingly, all mammalian, and most eukaryotic, cells have the machinery to splice exons into mRNA.

Gene trap vectors have been designed to integrate into genes in a manner that allows the cellular splicing machinery to splice vector encoded exons to cellular mRNAs. Commonly, gene trap vectors contain selectable marker sequences that are preceded by strong splice acceptor sequences and are not preceded by a promoter. Thus, when such vectors integrate into a gene, the cellular splicing machinery splices exons from the trapped gene onto the 5' end of the selectable marker sequence. Typically, such selectable marker genes can only be expressed if the vector has integrated into a gene with an active promoter. The resulting gene trap events are subsequently identified by selecting for cells that can survive selective culture. Thus, not only does the insertion of the gene trap vector create a mutation in the trapped gene, it also provides a molecular tag for ease of identifying the gene that has been trapped. Common gene identification protocols used to obtain sequences from fusion transcripts include 5' RACE, cDNA cloning, and cloning of genomic DNA surrounding the site of vector integration. However, these methods have proven labor intensive, not readily amenable to automation, and generally impractical for high-throughput. Moreover, such methods exclude the study of transcriptionally silent genes.

Other vectors have been developed that rely on a selectable marker gene preceded by a promoter and followed by a splice donor sequence instead of a polyadenylation sequence. However, these vectors do not result in expression of the selection marker unless they integrate into a gene and subsequently trap downstream exons which provide a polyadenylation sequence. Integration of such vectors into the chromosome results in the splicing of the selectable marker gene to 3' exons of the trapped gene. These vectors do provide a number of advantages. They can be used to trap genes regardless of whether the genes are normally expressed in the cell type in which the vector has integrated. In addition, cells harboring such vectors can be selected and the trapped gene sequence can be identified using automated (e.g., 96-well plate format) gene identification assays such as 3' RACE (see generally, Frohman, 1994). Using these vectors it is possible to produce large numbers of mutations and rapidly identify the mutated, or trapped, gene.

Although the use of ES cells in which genes have been trapped or inactivated is a powerful way to rapidly perform gene targeting for testing in a whole organism, e.g., a transgenic mouse (see Zahnbrowicz et al., 1998; Wiles et al., 2000), this method is limited because the gene is irreversibly inactivated in the ES cells. And although it is very useful to have the capability to knock out or inactivate a gene, the inactivation of many genes will be lethal or result in developmental adaptations. To individually target genes by homologous recombination and allow for conditional control of gene inactivation, recombinase/recognition site techniques, e.g., Cre-lox, have been used so that the resulting mice undergo site-specific recombination in a tissue-specific or temporally controlled manner. However, the production of mice with the conditional knockout is even more time-consuming and expensive than the production of traditional knockout mice. Moreover, the process of targeting requires extensive knowledge of the structure of a gene, a partial clone of the targeted gene, precise placement of recombinase recognition sites, and entails extensive manipulation of mouse genomic DNA.

Thus, what is needed is a high-throughput method to prepare a library of cells in which each cell in the library contains a gene that can be inactivated in a conditional, e.g., temporally- or spatially-controlled, manner. What is also needed is a rapid and efficient method to prepare targeting vectors for homologous recombination in a manner that results in a functional gene that can be disrupted in a conditional manner.

SUMMARY OF THE INVENTION

The invention provides recombinant vectors and methods of using the vectors in a high-throughput genetic system to rapidly generate conditional and/or conventional knockout mutants, e.g., mice, useful to identify and define mammalian gene function in vivo. The methods of the invention combine gene trapping, gene targeting, and site-specific recombination techniques. The vectors of the invention comprise a transcriptionally silent genetic element that is inserted within a gene in a target cell in a manner that retains the functionality of the gene, and which element can be manipulated to inactivate the gene when desired. The vectors of the invention may be introduced to cells via any means including non-biological means, e.g., electroporation, or biological means, e.g., via infection with a viral vector such as a retroviral vector.

As described hereinbelow, in one embodiment, the vector comprises a gene trap cassette and a mutational element cassette that is transcriptionally silent, but which can be activated by recombinase expression to disrupt expression of the trapped gene, e.g., in one embodiment electroporation is employed with a "Double Switch" vector and in another embodiment transduction of a "Double Flip" vector is employed (FIG. 1). The mutational element cassette comprises operably linked: i) a first site-specific recombination sequence for a first recombinase; ii) a mutational sequence which comprises a splice acceptor sequence linked to a first marker gene linked to a polyadenylation sequence; and iii) a second site-specific recombination sequence for the first recombinase, e.g., in opposite orientation to the first site-specific recombination site. A site-specific recombination system has three elements: a pair of DNA sequences (the site-specific recombination sequences) and an enzyme (the recombinase) which only catalyzes recombination events between the two site-specific recombination sequences. The gene trap cassette comprises operably linked: i) a first site-specific recombination sequence for a second recombinase; ii) a first gene trap element comprising a first promoter operably linked to a second marker gene operably linked to a splice donor sequence; and (iii) a second site-specific recombination sequence for the second recombinase. Optionally, a second gene trap element, which may be used to identify whether the vector has inserted into an intron or an exon, is included in the gene trap cassette, which second gene trap element comprises a second promoter operably linked to a nucleotide sequence and does not include a splice donor. In one embodiment, the mutational sequence is inverted relative to the gene trap cassette.

It is preferred that the second marker gene is a selectable marker gene, although any marker gene may be employed as the second marker gene, e.g., a marker conferring antibiotic resistance, an enzymatic marker, and a fluorescently detectable marker. Preferably, the first marker gene is a screenable gene, e.g., one which does not require disruption of cell membranes, although any marker gene may be employed as the first marker gene. In one preferred embodiment, the mutational sequence comprises a splice acceptor sequence linked to an internal ribosome entry site (IRES) operably linked to the first marker gene. Preferably, the site-specific recombination sequences which flank the mutational sequence are sequences which undergo an irreversible reaction such as mutant lox sites, e.g., mutant loxP sites (Albert et al., 1995; Araki et al., 1992), which are recognized by cre-recombinase. It is also preferred that the gene trap element(s) is flanked by a pair of FRT sites which are recognized by FLP recombinase. The site-specific recombination sites which flank the gene trap element are preferably in the same relative orientation so as to effect a deletion of the intervening sequence. Preferably, a protection sequence (PS) is added to the 5' end of the mutational cassette to protect the vector splice acceptor sequence from endonuclease digestion. In one embodiment of the invention, the genetically engineered vector is a viral vector, e.g., a retroviral, lentiviral, adenoviral or herpesviral vector, and the mutational element cassette in this embodiment of the vector of the invention is in the same orientation as the gene trap cassette. When employing a viral vector, e.g., a retroviral vector, an additional site-specific recombination site such as a FRT site is optionally added between the 5' end of the vector and the first recombination site, for instance in a retroviral vector, the additional recombination site is added between the 3' LTR and loxP site, in which the orientation of the FRT sequence is opposite to the pair of FRT sites that flank the gene trap cassette.

The introduction of the vector into a host cell, e.g., a prokaryotic cell or a eukaryotic cell such as a plant cell or a vertebrate cell such as a mammalian cell, may be accomplished by any method to yield a genetically altered cell. The expression of the marker gene in the gene trap cassette in the genetically altered cell allows the selection of clones with trapped genes and the identification of the trapped gene, e.g., by rapid amplification of cDNA ends (3' RACE). The gene trap element can be removed in cells, e.g., following selection, by introducing the appropriate recombinase to the cell. For instance, by introducing the recombinase or DNA encoding the recombinase to the cell comprising the vector, the trapped gene is rendered functional (first switch). Moreover, vector insertion within an exon may result in disruption of the trapped gene even after recombinase-mediated excision of the gene trap element. To identify exonal insertion events, a second gene trap element may be employed. The second gene trap element which lacks splice acceptor and splice donor sequences is preferably located 3' to the first gene trap element splice donor sequence and comprises a promoter operably linked to a nucleotide sequence which is unique to the vector relative to the host cell genome into which the vector is introduced. Thus, if the vector inserts into an exon, the expression of the second gene trap element produces a RNA comprising the unique sequence followed by sequence from the endogenous exon, whereas if the vector inserts into an intron, the unique sequence will not be spliced into the gene mRNA. RT-PCR with a primer that binds to the unique sequence permits the identification and sequencing of the cDNA to determine exonal integration.

Cells that have undergone the first switch to reactivate the trapped gene can be employed to prepare cells in which the mutational sequence inverts (second switch), e.g., in the presence of the appropriate recombinase, preferably irreversibly, so that the first marker gene can be expressed. For example, ES cells that have undergone the first switch may be used to generate mice containing a silent mutational element cassette upstream of the deleted gene trap element. Breeding of homozygous mice created from those ES cells to mice expressing the first recombinase in a tissue-specific or inducible manner will result in inversion of the mutational sequence and a disruption of the trapped gene (second switch). In particular, the vectors of the invention are useful to construct a library of cells with insertions in individual genes, preferably cells that are available for the production of mice with conditional gene knockouts or knock-ins. Knockins can be prepared by inserting the cassette with the mutational element aligned in the same orientation as the first gene trap cassette. Recombinase-mediated inversion of the mutational element results in transcriptional silencing of the mutational element and restores (rescues) gene function. Moreover, these ES cells can also be used to generate conventional knockout mice by inversion of the mutational sequence in vitro. Individual clones of genetically altered cells may be isolated.

Thus, the method of the invention greatly facilitates the investigation of the function of individual genes by a rapid extension of the conditional knockout approach to the entire mammalian genome. The benefits of this approach include the potential to discover novel phenotypes and create useful in vivo model systems for the study of disease. The strategy is particularly well suited for studying embryonic development. Moreover, because the inactivation of many genes will be lethal or result in developmental adaptations, it is very useful to have the capability to inactivate or "knockout" a gene in an animal in a temporally or spatially controlled (conditional) manner. Thus, the invention provides a method for random insertional and conditional mutagenesis of genes.

In one embodiment, the method comprises random insertion of genetic elements into mammalian cells, e.g., rodent or human ES cells, to prepare a library of mammalian cells with inserted genetic elements that yield a null allele using a double switch process. The introduction of a site-specific recombinase results in the reactivation of the normal gene (first switch). A library of such cells, for instance, murine ES cells, with insertions in individual genes is then available for the production of mice with conditional gene knockouts or knockins. These mice are bred to mice which express the appropriate recombinase, or may be otherwise contacted with the recombinase. In the presence of the recombinase, the silent mutational sequence is activated (inverted) so as to disrupt the gene into which the sequence in inserted (second switch).

Also provided is a genetically engineered vector comprising a mutational element cassette comprising operably linked: i) a site-specific recombination sequence for a selected recombinase; ii) a mutational sequence which comprises a splice acceptor sequence linked to a marker gene linked to a polyadenylation sequence, which mutational sequence is not expressed in a host cell as the orientation of the mutational sequence is inverted relative to the promoter of the host cell gene into which the vector is inserted; and iii) a further site-specific recombination sequence for the selected recombinase.

Further provided is a transgenic mouse, the genome of which is augmented with a recombinant DNA comprising a mutational sequence comprising a splice acceptor sequence linked to a first marker gene linked to a polyadenylation sequence, which mutational sequence is in the same orientation as the endogenous gene into which the recombinant DNA is inserted. The transgenic mouse has at least one phenotypic difference associated with the recombinant DNA relative to a transgenic mouse comprising the recombinant DNA in which the mutational sequence is inverted. In one embodiment, the "Double Flip" vector shone in FIG. 1 for retroviral infection disrupts the endogenous gene in ES cells when it inserts into the genome, since the mutational element has the same orientation as the trapped gene. Transfection of ES cells with FRT recombinase allows selection of clones in which the gene trap element has been excised and the mutational cassette has been inverted, resulting in a functional allele (first switch). When crossed with a mouse expressing Cre recombinase under tissue-specific and/or temporal control, the presence of Cre recombinase results in inversion of the mutational cassette (second switch) and gene disruption.

Also described herein is a rapid and efficient method that greatly simplifies the production of vectors for conditional gene targeting (Universal. "Flipout" vector). Thus, in this embodiment of the invention, the vector is a homologous recombination targeting vector for conditional gene inactivation. The method allows the construction of gene targeting vectors for any gene by performing routine PCR and vector ligation. A transcriptionally silent, mutational element within the targeting vector is activated by a recombinase, thereby allowing spatial and/or temporal control of gene inactivation. As described hereinbelow, the method employs a genetically engineered vector comprising a mutational sequence that is transcriptionally silent but can be inverted to truncate and inactivate a targeted gene in a conditional manner. The vector comprises operably linked: a mutational element cassette and preferably two selectable marker cassettes for positive and negative selection. The mutational element cassette comprises operably linked: i) a first site-specific recombination sequence for a first recombinase; ii) a mutational sequence which comprises a splice acceptor sequence linked to a first marker gene linked to a polyadenylation sequence; and iii) a second site-specific recombination sequence for the first recombinase. The positive selectable marker cassette comprises operably linked: i) a first site-specific recombination sequence for a second recombinase; ii) a first promoter operably linked to a second marker gene; and (iii) a second site-specific recombination sequence for the second recombinase. The mutational sequence is inverted relative to the second marker gene.

It is preferred that the second marker gene is a selectable marker gene, although any marker gene may be employed as the second marker gene, e.g., a marker conferring antibiotic resistance, an enzymatic marker, and a fluorescently detectable marker. Preferably, the first marker gene is a screenable gene, e.g., one which does not require disruption of cell membranes, although any marker gene may be employed as the first marker gene. In one embodiment, the mutational sequence comprises a splice acceptor sequence linked to an IRES operably linked to the first marker gene. Preferably, the site-specific recombination sequences which flank the mutational sequence are sequences which undergo an irreversible reaction such as mutant lox sites, e.g., mutant loxP sites, and those that flank the selectable marker cassette FRT sites which are recognized by FLP recombinase.

It is preferred that a negative selectable marker gene, for example, the HSV-tk gene, is engineered into the vector to delete clones in which random integration of the vector has occurred. It is also preferred that one multicloning site (MCS) is linked to the 5' end of the mutational element and another multicloning site is linked to the 3' end of the positive selection marker. In one embodiment, the MCS is comprised of relatively unique restriction sites such as Sgf I, Srf I, Not I, Pme I, Fse I, Asc I, and/or Pac I.

Thus, the invention provides a gene targeting vector comprising a transcriptionally silent, mutational element within the targeting vector that is activated under control of a recombinase, thereby allowing spatial and temporal control of gene activation. Because the mutational cassette is self-contained and transcriptionally silent until activated, the invention obviates the laborious subcloning and precise placement of recombinase recognition sites currently required to create a gene targeting vector for conditional mutation, allowing the simple insertion of sequences upstream and downstream of the desired site of gene truncation. Thus, a conditional targeting vector can be simply constructed for any gene by determining an intron and the flanking sequences within the gene, the targeting vector allows insertion of the cassette in this intron and subsequent gene truncation and inactivation when desired. The invention also describes a method of preparing that vector, e.g., using routine molecular biological techniques such as PCR and DNA ligation, and a method of using such a vector.

BRIEF DESCRIPTION OF THE FIGURES

FIG. 4B is a schematic of a "flipout" gene targeting vector of the invention and the molecular structure of the vector after a first and then a second recombination event.

DETAILED DESCRIPTION OF THE INVENTION

Definitions

Figure 1A:
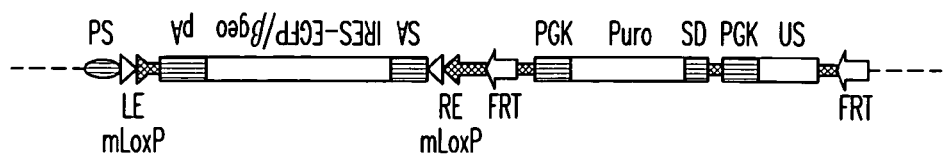
FIG. 1A is a schematic of "Double Switch" and "Double Flip" gene trap vectors of the invention. PS=protected sequence; PGK=phosphoglycerol kinase promoter; puro=puromycin resistance gene; SA=splice acceptor; SD=splice donor; pA=polyadenlyation sequence; mLoxP=mutant loxP site; FRT=Flp-recombinase recognition sequence; IRES=internal ribosome entry site; EGFP/beta-geo=enhanced Green Fluorescent Protein and beta-galactosidase-neomycin phosphotransferase fusion gene; US=a unique sequence (relative to the genome of the target host cell) that permits the determination of whether the cassette is integrated into an exon or an intron. Integration into an exon may be mutational and not conditional. Mutant LoxP sites are indicated by the black arrowhead.
Figure 1A:
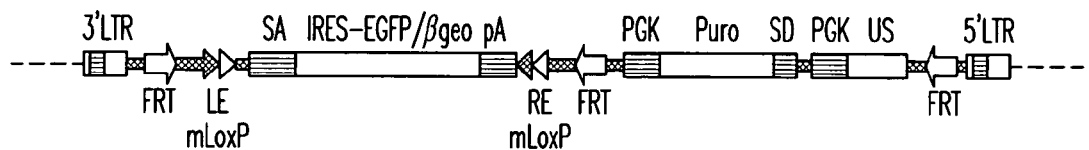
Figure 1B:
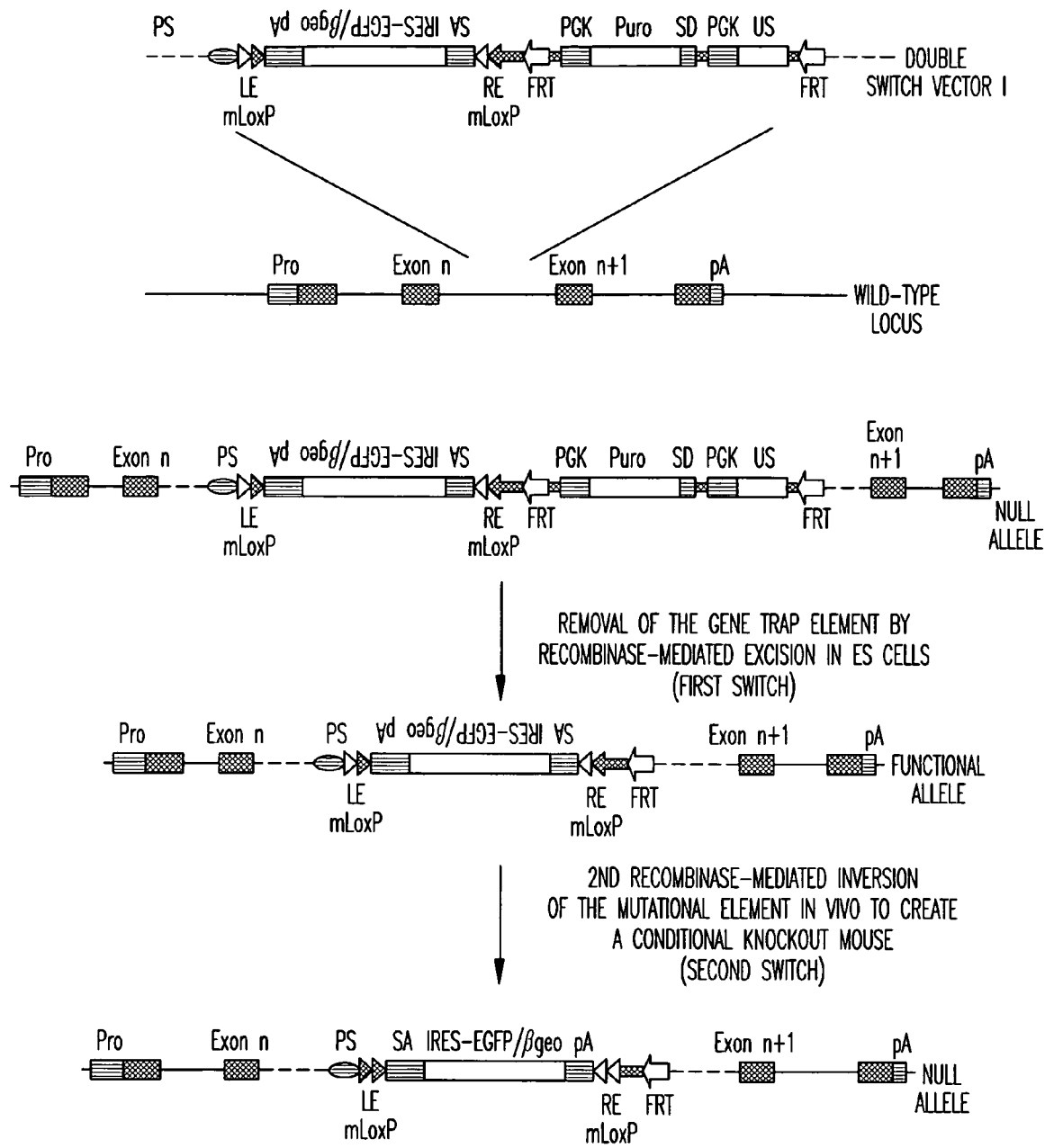
FIG. 1B is a schematic of the "Double Switch" gene trap vector of the invention which optionally includes a second gene trap cassette, and the molecular structure of the vector after the first and second recombination event (switch).
Figure 1C:
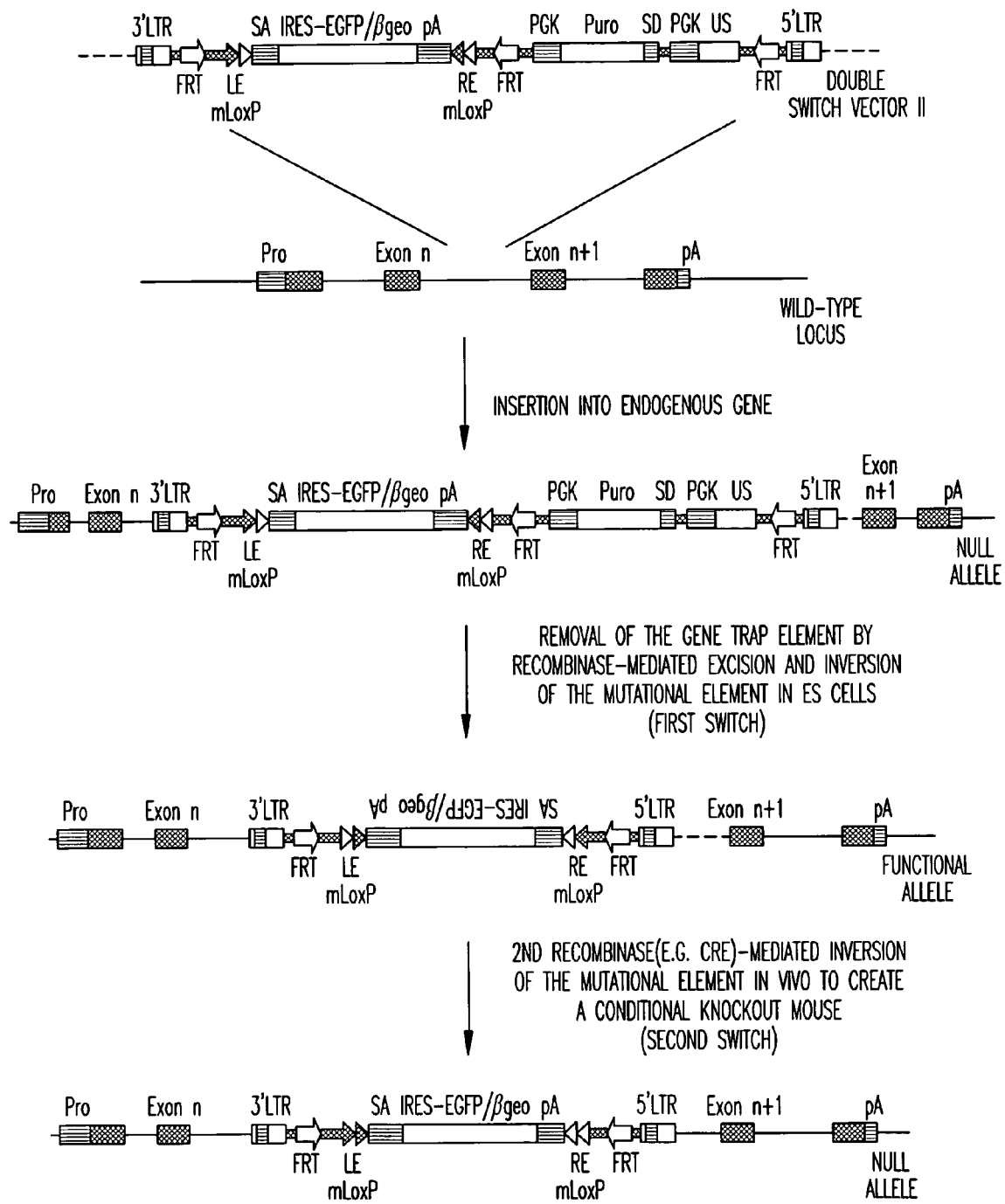
FIG. 1C is a schematic of the "Double Flip" gene trap vector of the invention, and the molecular structure of the vector after the first and second recombination event (switch).
Figure 2A:
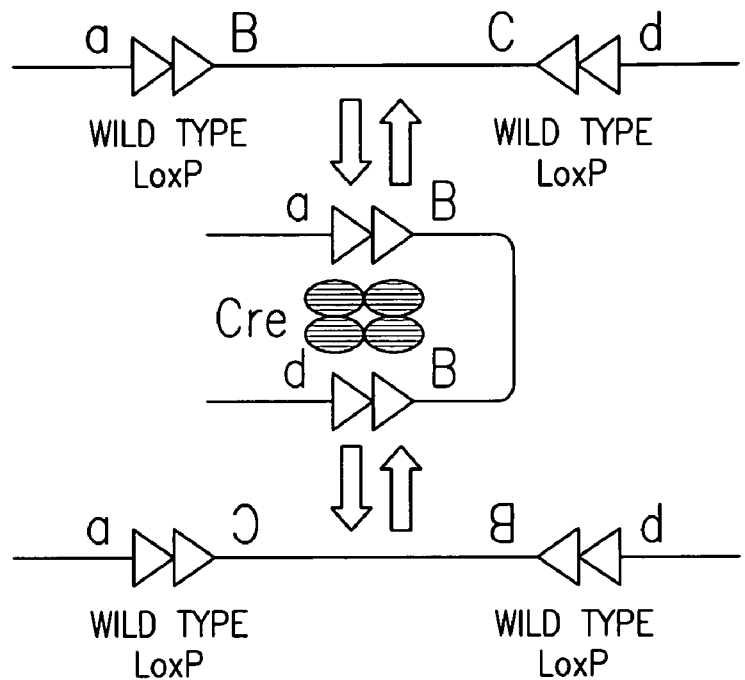
FIG. 2 is a schematic of the structure of Cre-recombinase mediated inversion of wild type (A) and mutant (B) loxP sites.
Figure 2B:
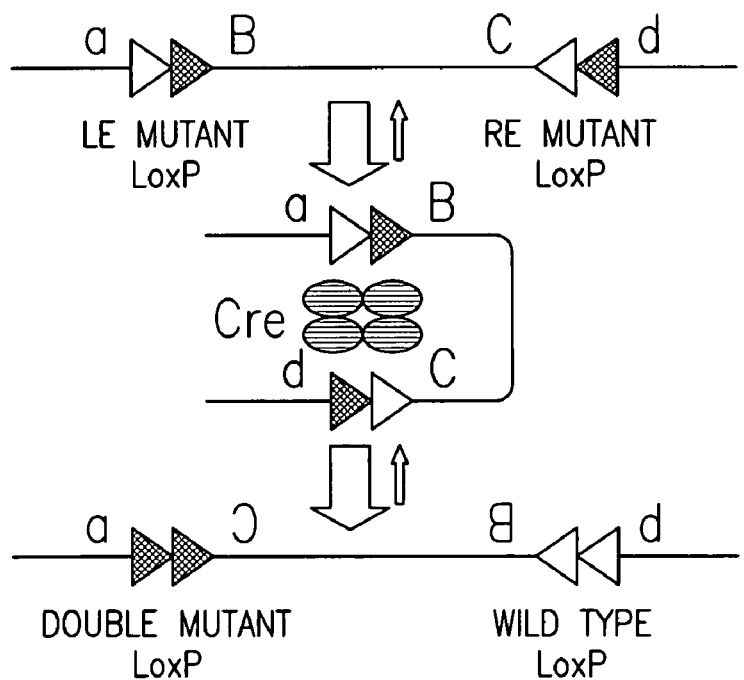

As used herein, a "genetically modified", "genetically altered" or "transgenic" cell means a cell, the genome of which comprises a recombinant DNA molecule or sequence ("transgene"), e.g., a vector or construct, which is introduced into the genome of the cell by transformation. The term "wild type" refers to an untransformed cell, i.e., one where the genome has not been altered by the presence of the recombinant DNA molecule or sequence.

As used herein, the terms "isolated and/or purified" refer to in vitro preparation, isolation and/or purification of a DNA molecule, sequence or segment, so that it is not associated with in vivo substances.

As used herein, "site-specific recombination" is intended to include the following three events: 1) deletion of a target DNA segment flanked by site-specific recombination sites or sequences, e.g., lox sites; 2) inversion of the nucleotide sequence of a target DNA segment flanked by site-specific recombination sites or sequences, e.g., lox sites; and 3) reciprocal exchange of target DNA segments proximate to site-specific recombination sites or sequences, e.g., lox sites located on different DNA molecules. Site-specific recombinase systems include, but are not limited to, the Cre/lox system of bacteriophage P1 (U.S. Pat. No. 5,658,772), the FLP/FRT system of yeast (Golic and Lindquist, 1989), the Gin recombinase of Mu (Maeser et al., 1991), the Pin recombinase of E. coli (Enomoto et al., 1983), and the R/RS system of the pSR1 plasmid (Araki et al., 1992).

To remedy the reversibility of a site-specific recombination reaction, the structure of the recombination system may be altered. The site-specific recombination sequence can be mutated in a manner that the product of the recombination reaction is no longer recognized as a substrate for the reverse reaction, thereby stabilizing the integration or excision event. For example, to remove marker genes, such as those that confer antibiotic resistance in transgenic cells, lox sites in the same orientation are positioned to flank the marker gene. Removal of the marker can also allow the use of the same marker in a second transformation of the transgenic cell. Or a DNA sequence that regulates expression of a gene can be excised resulting in altered, e.g., increased or decreased, expression of the gene.

Other lox sites include loxB, loxL, and loxR sites which are nucleotide sequences isolated from E. coli (Hoess et al., 1982). Lox sites can also be produced by a variety of synthetic techniques which are known in the art. For example, synthetic techniques for producing lox sites are disclosed by Ito et al. (1982) and Ogilvie et al. (1981).

As used herein, the expression "lox site" means a nucleotide sequence at which the gene product of the cre gene can catalyze a site-specific recombination. LoxP is a 34 base pair nucleotide sequence which can be isolated from bacteriophage P1 by methods known in the art (see, for example, Hoess et al., 1982). LoxP consists of two 13 base pair inverted repeats separated by an 8 base pair spacer region. As used herein, the expression "cre gene" means a nucleotide sequence which codes for an enzymic gene product which effects site-specific recombination of DNA in eukaryotic cells at lox sites. A cre gene can be isolated from bacteriophage P1 by methods known in the art (see Abremaid et al., 1983).

"Control sequences" is defined to mean DNA sequences necessary for the expression of an operably linked coding sequence in a particular host organism. Eukaryotic cells are known to utilize promoters, polyadenylation signals, and enhancers.

"Operably linked" or "operably positioned" is defined to mean that the nucleic acids are placed in a functional relationship with another nucleic acid sequence. For example, DNA for a presequence or secretory leader is operably linked to DNA for a peptide or polypeptide if it is expressed as a preprotein that participates in the secretion of the peptide or polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accord with conventional practice.

For the purposes of the present invention the term "gene" shall refer to any and all discrete coding regions of the cell's genome, as well as associated noncoding and regulatory regions. Additionally, the term operatively positioned shall refer to the fact that the control elements or genes are present in the proper orientation and spacing to provide the desired or indicated functions of the control elements or genes. Also for the purposes of the present invention, a gene is "expressed" when a control element in the cell mediates the production of functional or detectable levels of mRNA encoded by the gene, or a selectable marker inserted therein. A gene is not expressed where the relevant control element in the cell is absent, has been inactivated, or does not mediate the production of functional or detectable levels of mRNA encoded by the gene, or a selectable marker inserted therein.

The Vectors of the Invention

The invention is directed to the use of vectors to conditionally disrupt a functional gene in a eukaryotic cell. The size of the human genome as well as those of most other mammals is in the range of $3 \times 10^9$ base pairs. The currently estimated maximal number of genes within a mammalian genome is in the order of around 100,000. Of the genes identified thus far and analyzed, the average size is 16.6 kb, of which 2.2 kb is the average size of the mature mRNA. Thus, intron sequences which are non-coding make up the vast majority of the size of genes (about 87%) and are the likely sites of integration of molecular tags that integrate at random (Casadaban and Cohen 1979; Chu and Sharp 1981; Weber at al 1984).

The vectors exploit the process of RNA splicing, by inserting two different molecular tags resembling exons at a random location in the genome. One of the tags is a promoterless (first) marker, e.g., reporter, gene, linked to a functional splice acceptor sequence, so that its expression is dependent on cellular promoters (the mutational sequence). This implies that the tag integrated into an active chromosomal locus. For example, Gossler et al. (1989) used the bacterial β-galactosidase gene as a reporter engineered downstream of the splice acceptor consensus sequence derived from the mouse engrafted locus. Introduction of this splice acceptor-reporter construction into mouse ES cells was performed to identify genes that were active in ES cells. Upon introduction of ES cells expressing the reporter gene into recipient embryos to generate chimeras, expression of the reporter gene gave information as to the temporal and spatial pattern of expression of the locus of integration (Gossler et al, 1989). Friedrich and Soriano (1991) employed a vector encoding a fusion protein including β-galactosidase and neomycin phosphotransferase. This fusion protein gene was linked to the adenovirus splice acceptor and was introduced to ES cells (Friedrich and Soriano, 1991).

Moreover, the mutational sequence of the invention comprises a polyadenylation sequence linked to the first marker gene. In the proper orientation, i.e., relative to an endogenous promoter, a transcript initiated 5' to the mutational sequence will be spliced to the first marker gene and terminated by the polyadenylation sequence in the mutational sequence. Preferably, a IRES is operably positioned in the mutational cassette (5' to the marker gene open reading frame) to permit independent expression of the marker gene, i.e., not as a fusion protein. When the mutational sequence is inverted relative to endogenous promoter, no expression of the first marker gene occurs. Alternatively, the first marker, which is downstream of an IRES, is expressed if the vector integrates into a downstream exon, after the appropriate recombinase inverts the cassette comprising the splice acceptor sequence and the marker gene.

The other tag comprises a promoter and a second (different) marker gene linked to a splice donor sequence (the first gene trap element), as well as a promoter followed by a transcriptional start site and, for the second gene trap element, a promoter linked to a unique nucleotide sequence. After integration of this tag into the genome, a transcript initiated at the first promoter yields a chimeric transcript comprising the marker gene spliced to an exon of the gene into which the tag is integrated and its endogenous polyadenylation sequence. The second promoter yields a transcript with a unique 5' sequence that is used to determine whether the vector has inserted into an exon, by generating a transcript with the unique sequence contiguous with the endogenous gene sequence 3' to the vector insertion. In another embodiment, the tag comprises a promoter and a second (different) marker gene linked to a polyA site.

Since knockout of the expression of essential or tissue-specific genes is desirable, certain vector sequence are flanked with recombinase sites such as those recognized by the FLP or CRE recombinases. The addition of the corresponding recombinase in cells or in the organism, e.g., via introduction of the recombinase or DNA which encodes the recombinase, allows the removal or inversion of certain vector sequences. The recombinase gene can be expressed from an independent expression cassette, e.g., introduced to a cell comprising vector sequences or by breeding a transgenic animal with vector sequence to an animal which expresses the recombinase. A recombinase which is expressed in a tissue-specific or regulatable manner inverts the sequence between the sites resulting in tissue-specific or regulatable expression of the host gene linked to the vector sequence.

Examples of sites recognized by recombinase include frt sites or loxP sites, respectively, identified by FLP and CRE recombinases. These recombination sites can be used to create chromosomal rearrangements such as inversions, deletions and translocations. Thus, the presently described vectors are particularly useful for studying gene function through chromosomal rearrangements. Two or more such systems may be employed in the practice of the invention as long as each system is independent of the other.

For the gene trap or selectable marker cassette, the site-specific recombination system is employed to remove the gene trap or selectable marker element, leaving a single copy of the site-specific recombination sequence. For the mutational element cassette, the site-specific recombination system is employed to invert the mutational sequence. To result in the stable (long-term) expression of the first marker gene, the recombination reaction leading to a product where the first marker gene is in the same orientation as an endogenous promoter, is preferred over the reaction leading to a product where the first marker gene is in the opposite orientation as the endogenous promoter.

The present vectors are preferably engineered to encode and express at least two marker genes, and more preferably three (for gene targeting vectors), that facilitate the identification of target cells that incorporate the vector sequences of the invention. Such markers include, but are not limited to, antibiotic resistance genes, calorimetric marker genes, enzymes (e.g., β-lactamase), or other marker genes that, for example, mediate the direct or indirect expression of fluorescent marker genes such as the gene encoding green fluorescent protein, and assays for detecting the same, which are described, e.g., in U.S. Pat. No. 5,625,048. For the purposes of the present disclosure, the term "directly," when used in a biological or biochemical context, refers to direct causation of a process that does not require intermediate steps, usually caused by one molecule contacting or binding to another molecule (which can be a molecule of the same type or a different type of molecule). For example, molecule A contacts molecule B, which causes molecule B to exert effect X that is part of a biological process. For the purposes of the present invention, the term "indirectly," when used in a biological or biochemical context, refers to indirect causation that requires intermediate steps, usually caused by two or more direct steps. For example, molecule A contacts molecule B to exert effect X which in turn causes effect Y.

Marker genes are well known to the art and include but are not limited to the neomycin phosphotransferase, hygromycin phosphotransferase and puromycin phosphotransferase genes. Expression of such positive selectable marker genes is made detectable by supplementing the culture medium with the corresponding drug, G418, hygromycin and puromycin, respectively, and genes that encode resistance to tetracycline, ampicillin and kanamycin. Further positive selectable markers include but are not limited to histidinol-dehydrogenase, chloramphenicol-acetyl transferase (CAT), dihydrofolate reductase (DHFR), and hypoxanthine guanine phosphoribosyl transferase (HPRT) for selection of HPRT-cells in medium supplemented with hypoxanthine, aminopterine and thymidine (HAT). Negative selection markers include HPRT, gpt, HSV-tk, diphtheria toxin, ricin toxin and cytosine deaminase.

The expression of positive selectable marker genes can be detected, using a fluorescent activated cell sorter (FACS) for observing emission of light of a specific wave length. For example, a protein that spontaneously emits light and can serve as reporter as well as a positive/negative reporter selectable marker in FACS analysis, is the green fluorescent protein (GFP) isolated from the bioluminescent jellyfish *Aequorea victoria*. FACS analysis and FACS sorting make it possible to isolate cells that emit light as well as those that do not. For example, the selectable marker gene can include the bacterial β-galactosyltransferase which could be used in combination with a vital stain consisting of a fluorescent dye whose emission spectrum could depend on cleavage of a β-glycosidic structure. Subsequent to staining of live cells with the substrate for β-galactosidase, FACS analysis would be employed preferentially to isolate either expressing or non-expressing cells. Other detectable markers include alkaline phosphatase.

Selectable markers include genes that allow for identification, selection and/or sorting of cells based upon cell surface expression of proteins that normally would not be expressed and would not interfere or adversely affect the biological properties of the cells. Suitable selectable marker genes include cell-cell and cell-substrate adhesion molecules including ICAMs, integrins, cadherins or selectins that normally are not expressed on the cell of interest, and which do not cross-react with endogenous ligands. Expression of such markers can be detected using specific antibodies, or other forms of natural ligands, in combination with sorting protocols including panning or FACS. In one example, the marker includes a truncated form of a heterologous IL-3 receptor (swine form in mouse cells, human form in swine cells) that is incapable of transducing a signal into the cell. Expression of this receptor is then monitored using the natural ligand (swine or human IL-3) which is preferably conjugated with a fluorescent dye or an enzyme that detectably converts a chromogenic substrate.

Positive selection is preferably achieved using cell-substrate adhesion molecules including integrins that normally are not expressed by the biological system, i.e., in the cell types of interest such as the mouse embryonic stem cells, miniature swine embryonic stem cells as well as mouse, porcine and human hematopoietic stem cells.

Other molecules useful as selectable genes include glycosyltransferases of a defined specificity that can be assayed, and enzymes involved in post-translational processing of polypeptides that confer dominant effects, like attachment of oligosaccharide chains by glycosyltransferases.

Preferred promoters for use in the vector of the invention are those that are active in the host cell to be transformed. For example the vector may itself comprise a promoter that is active in mammalian cells, or may utilize a promoter already present in the genome that is the transformation target. Any number of transcriptional promoters and enhancers may be incorporated into the vector including, but not limited to, the herpes simplex thymidine kinase promoter, cytomegalovirus (CMV) promoter/enhancer, SV40 promoters, pgk promoter, pga promoter, regulatable promoters (e.g., metallothionein promoter), adenovirus late promoter, retroviral LTR, vaccinia virus 7.5K promoter, and the like, although many other promoter elements well known to the art may be employed in the practice of the invention (see generally, Sambrook et al., 1989) and Ausubel et al. (1989).

Promoter/enhancer regions can also be selected to provide tissue-specific expression. For example, to express a recombinase in a tissue-specific manner, a tissue-specific promoter may be employed.

Other elements functional in the host cells, such as and the like, may also be a part of the vector. Such elements may or may not be necessary for the function of the DNA, but may provide improved expression of the DNA by affecting transcription, stability of the mRNA, or the like. Such elements may be included in the DNA as desired to obtain the optimal performance of the transforming DNA in the cell.

To prepare vectors for transformation herein, the recombinant DNA may be circular or linear, double-stranded or single-stranded. A DNA sequence which encodes an RNA sequence that is substantially complementary to a mRNA sequence encoding a gene product is typically a "sense" DNA sequence cloned into a cassette in the opposite orientation (i.e., 3' to 5' rather than 5' to 3'). Generally, the recombinant DNA sequence is in the form of chimeric DNA, such as plasmid DNA. As used herein, "chimeric" means that a vector comprises DNA from at least two different species, or comprises DNA from the same species, which is linked or associated in a manner which does not occur in the "native" or wild type of the species.

The general methods for constructing recombinant DNA which can transform target cells are well known to those skilled in the art, and the same compositions and methods of construction may be utilized to produce the DNA useful herein. For example, Sambrook et al. (1989) provides suitable methods of construction.

The recombinant DNA can be readily introduced into the host cells, e.g., mammalian, bacterial, yeast or insect cells by any procedure useful for the introduction into a particular cell, e.g., physical or biological methods, to yield a transformed cell having the recombinant DNA stably integrated into its genome, so that the DNA molecules, sequences, or segments, of the present invention are expressed by the host cell. The host cells of the present invention are typically produced by transfection with a DNA sequence in a plasmid expression vector, a viral expression vector, or as an isolated linear DNA sequence. The presently described vectors can be introduced to target cells by any of a wide variety of methods known in the art.

Physical methods to introduce a preselected DNA into a host cell include transfection, e.g., using calcium phosphate precipitation, lipofection, particle bombardment, microinjection, electroporation, and the like. Electroporation is a feasible approach for delivery to certain types of cells including embryonic stem cells or hematopoietic stem cells. Generally, the efficiency of generating stable transformants of eukaryotic cells is somewhat lower than with viral vectors, but is preferable in cases where the cells are refractory to viral infection or integration of the provirus into the host chromosome.

Lipofection can also be used so that the vector will become translocated across the plasma and nuclear membrane for stable integration into random sites of the chromosomes from cell types that are permissive for lipofection, including mouse embryonic stem cells.

Biological methods to introduce the DNA of interest into a host cell include the use of DNA and RNA viral vectors. The main advantage of physical methods is that they are not associated with pathological or oncogenic processes of viruses. However, they are less precise, often resulting in multiple copy insertions, random integration, disruption of foreign and endogenous gene sequences, and unpredictable expression. Viral vectors, and especially retroviral vectors, have become the most widely used method for inserting genes into mammalian, e.g., human cells. Other viral vectors can be derived from poxviruses, herpes simplex virus I, adenoviruses and adeno-associated viruses, and the like.

As used herein, the term "host cell" is intended to include any cell including primary cells as well as well-characterized homogenous, biologically pure populations of cells (cell lines). Preferably, the vectors of the invention can be used in virtually any type of eukaryotic cell that can be manipulated to insert vector sequences into the genome of the cell. For example, the vectors may be used in primary animal tissues as well as any other eukaryotic cell or organism including, but not limited to, yeast, molds, insects, fungi, and plants. Preferably the host cell is of mammalian origin. Additional examples of suitable target cells include, but are not limited to, canine, bovine, equine, feline, ovine, caprine, porcine, murine and human cells, as well as endothelial cells, epithelial cells, islets, neurons or neural tissue, mesothelial cells, osteocytes, lymphocytes, chondrocytes, hematopoietic cells, immune cells, cells of the major glands or organs (e.g., lung, heart, stomach, pancreas, kidney, skin, and the like), exocrine and/or endocrine cells, embryonic and other stem cells, fibroblasts, and culture adapted and/or transformed versions of the above. Preferred cells for use with the vector of the invention include cells which can give rise to differentiated cells and more preferably to all cells in an organism, e.g., a fertilized oocyte or an embryonic stem cell.

"Transfected" or "transformed" is used herein to include any host cell or cell line, the genome of which has been altered or augmented by the presence of at least one preselected DNA sequence, which DNA is also referred to in the art of genetic engineering as "heterologous DNA," "recombinant DNA," "exogenous DNA," "genetically engineered," "non-native," or "foreign DNA," wherein said DNA was isolated and introduced into the genome of the host cell or cell line by the process of genetic engineering.

To confirm the presence of the introduced DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular fusion polypeptide, e.g., by immunological means (ELISAs and Western blots) or by assays described hereinabove to identify agents falling within the scope of the invention.

To detect and quantitate RNA produced from introduced DNA segments, RT-PCR may be employed. In this application of PCR, it is first necessary to reverse transcribe RNA into DNA, using enzymes such as reverse transcriptase, and then through the use of conventional PCR techniques amplify the DNA. In most instances PCR techniques, while useful, will not demonstrate integrity of the RNA product. Further information about the nature of the RNA product may be obtained by Northern blotting. This technique demonstrates the presence of an RNA species and gives information about the integrity of that RNA. The presence or absence of an RNA species can also be determined using dot or slot blot Northern hybridizations. These techniques are modifications of Northern blotting and only demonstrate the presence or absence of an RNA species.

While Southern blotting and PCR may be used to detect the introduced DNA segment in question, they do not provide information as to whether the DNA segment is being expressed. Expression may be evaluated by specifically identifying the peptide products of the introduced DNA sequences or evaluating the phenotypic changes brought about by the expression of the introduced DNA segment in the host cell.

In one preferred embodiment, the vector of the invention can be incorporated into a viral vector for efficient delivery to eukaryotic cells. The resultant recombinant vector can transduce dividing cells, and upon infection, can integrate its genome at random sites in chromosomal DNA of host cells. Suitable vectors that can be used in conjunction with the presently disclosed cassettes include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, particularly viral vectors suitable for modifying nonreplicating cells, and how to use such vectors in conjunction with the expression of polynucleotides of interest can be found in the book Viral Vectors: Gene Therapy and Neuroscience Applications Ed. Caplitt and Loewy, Academic Press, San Diego (1995). As used herein, the term "expression" refers to the transcription of the DNA of interest, and the splicing, processing, stability, and, optionally, translation of the corresponding mRNA transcript.

In a preferred embodiment, a retroviral vector is employed to deliver the sequences of interest to a host cell. An advantage of retroviral delivery systems over standard transfection protocols concerns not only the efficiency of delivering the trap, but also the mode of integration of the vector into the host genome. While standard transfections using linear or supercoiled plasmid DNA can cause genomic rearrangements at the locus of integration, possibly causing adverse effects, retroviruses usually integrate into the genome without causing such rearrangements.

A retroviral vector will have LTRs derived from one or several types of retroviruses, and the LTRs may be genetically modified to achieve desired properties in the cell type of interest such as in embryonic stem cell derived from mouse, pig or human, or a hematopoietic stem cell derived from various mammalian origins. One suitable vector displaying such properties is the retroviral vector PLNX (Miller and Rosman 1989) or derivatives thereof. The retroviral vector can also include regulatory elements suitable for propagation and selection in E. coli which include an origin of replication (ori) and an antibiotic resistance marker for selection ($Amp^R$).

Where retroviral vectors are used to deliver the vector sequence, the retroviral vectors can be used in conjunction with retroviral packaging cell lines such as those described in U.S. Pat. No. 5,449,614. Where non-mouse animal cells are to be used as targets for generating the described libraries, packaging cells producing retrovirus with amphotropic envelopes will generally be employed to allow infection of a broad range of host cells. Alternatively, such retroviral vectors can be packaged in conjunction with chimeric integrase molecules. Typically, the LTRs used in the construction of the packaging cell lines are self-inactivating. That is, the enhancer element is removed from the 3' U3 sequences such that the proviruses resulting from infection would not have an enhancer in either LTR. An enhancer in the provirus may otherwise affect transcription of the mutated gene or nearby genes.

An additional advantage of using viral, and particularly retroviral, infection (e.g., biological methods) to deliver recombinant viral vectors incorporating the vector sequence is that viral infection is more efficient than standard nonbiological methods of delivering genetic material to target cells. Where recombinant genetic material is delivered by retroviral infection, the recombinant RNA genome of the retrovirus is reverse transcribed within the target cell, and the retroviral integrase packaged within the infecting virus subsequently mediates the essentially random integration of the vector into the target cell genome. Accordingly, additional embodiments of the present invention include methods of inserting recombinant vectors that are mediated by integrase activities that are either exogenously added to the target cell, or do not naturally occur within the target cell.

Representative retroviral vectors that can be adapted to incorporate vector sequence are described, e.g., in U.S. Pat. No. 5,521,076.

Given the extensive number of genes that can be rapidly characterized using the present vectors, additional embodiments of the present invention include gene trapped libraries of cultured animal cells that stably incorporate at least one of the marker genes of the vector of the invention. The presently described libraries may be made by a process comprising the steps of treating (i.e., infecting, transfecting, retrotransposing, or virtually any other method of introducing polynucleotides into a cell) a population of cells to stably integrate a vector of the invention, identifying or otherwise selecting for stably transduced or transformed cells. In a preferred embodiment, the animal cell libraries comprise mammalian cells, and in a particularly preferred embodiment, the mammalian cells are ES cells, e.g., murine ES cells. Preferably, such libraries are constructed such that at least two cells in the library have a vector of the invention integrated at a different site in the genome, although multiple integration events are also contemplated.

In a preferred embodiment of the invention, the individual genetically altered cells in the library are separated and clonally expanded. The isolated and clonally expanded genetically altered cells are then analyzed to ascertain the host genomic sequences which flank the vector sequence.

Thus, the invention further provides for the sequencing of at least a portion of the host gene for each clone in the library. The resulting sequence database subsequently serves as an index for the library. In essence, every group of clonally expanded cells in the library is individually catalogued using the partial sequence information. The resulting sequence database can be used to identify the host gene, or, alternatively, represents a powerful tool for the identification of novel genes. Once identified, the corresponding genetically altered cell may be taken from the library and studied further as described below.

Preferably, the library of isolated cells, or individual cell types (e.g., ES cells) comprise a collection of at least about 50 different genetically altered cells, typically at least about 100, more typically, at least about 500, preferably at least about 1,000, more preferably at least about 5,000, specifically at least about 10,000, more specifically at least about 25,000, and even more specifically at least about 40,000 up to about 100,000 to 500,000 different lines or more.

Preferably, the genomes of the different genetically altered cells present in a given library are essentially identical (e.g., derived from a common source or inbred strain) except for the location of the inserted vector sequences.

The presently described invention also allows for large-scale genetic analysis of the genomes of any organism for which there exists cultured cell lines. The described libraries may be constructed from any type of cell that can be transfected by standard techniques or transfected with a recombinant vector. Accordingly, the presently described methods of making libraries of genetically altered animal cells are also broadly applicable to virtually any eukaryotic cells that may be genetically manipulated and grown in culture.

Where mouse ES cells are used to construct the library, and preferably early passage ES cells, the library becomes a genetic tool for the comprehensive study of the mouse genome. Since ES cells can be injected back into a blastocyst and incorporated into normal development and ultimately the germ line, the mutated ES cells of the library effectively represent collection of transgenic mouse strains (see generally, U.S. Pat. No. 5,464,764). The mutational sequence in these mice can be activated by contacting the mice with the appropriate recombinase and the resulting phenotype identified and characterized. The transgenic mice or their offspring having the phenotype associated with activation of the mutational sequence can subsequently be bred with other mouse strains, and, back crossed to produce congenic or recombinant congenic animals that allow for the evaluation of the gene trap mutation in different genetic backgrounds. A representative listing various strains and genetic manipulations that can be used to practice the above aspects of the present invention (including the ES cell libraries) is "Genetic Variants and Strains of the Laboratory Mouse" 3rd Ed., Vols. 1 and 2, 1996, Lyon et al., eds., Oxford University Press, NY, N.Y.

A similar methodology can be used to construct virtually any non-human transgenic animal (or animal capable of being rendered transgenic). Such nonhuman transgenic animals may include, for example, transgenic pigs, transgenic rats, transgenic rabbits, transgenic cattle, transgenic goats, and other transgenic animal species, particularly mammalian species, known in the art. Additionally, bovine, ovine, and porcine species, other members of the rodent family, e.g. rat, as well as rabbit and guinea pig and non-human primates, such as chimpanzee, may be used to practice the present invention. Moreover, the vectors of the invention may be employed to prepare transgenic plants, e.g., transgenic dicots or monocots.

Transgenic animals and cells produced using the presently described library and/or vectors are useful for the study of basic biological processes and diseases including, but not limited to, aging, cancer, autoimmune disease, immune disorders, alopecia, glandular disorders, inflammatory disorders, ataxia telangiectasia, diabetes, arthritis, high blood pressure, atherosclerosis, cardiovascular disease, pulmonary disease, degenerative diseases of the neural or skeletal systems, Alzheimer's disease, Parkinson's disease, asthma, developmental disorders or abnormalities, infertility, epithelial ulcerations, and viral and microbial pathogenesis and infectious disease. As such, the described animals and cells are particularly useful for the practice of functional genomics.

In addition to the study of diseases, the presently described methods, libraries, cells, and animals are equally well suited for identifying the molecular basis for genetically determined advantages such as prolonged life-span, low cholesterol, low blood pressure, resistance to cancer, low incidence of diabetes, lack of obesity, or the attenuation of, or the prevention of, all inflammatory disorders, including, but not limited to coronary artery disease, multiple sclerosis, rheumatoid arthritis, systemic lupus erythematosus, and inflammatory bowel disease.

The present invention is further illustrated by the following example, which is not intended to be limiting in any way whatsoever.

EXAMPLE 1

Gene Trap Vectors for Conditional Gene Inactivation

The vectors of the invention comprise a removable gene trap cassette and an inverted (silent) mutational sequence that can be conditionally activated. An exemplary vector is shown in FIG. 1.

Gene Trap Cassette

The gene trap cassette comprises a promoter (e.g., one functional in ES cells such as the phosphoglycerate kinase-1 (PGK) promoter operably linked to a selectable marker gene (e.g., the puro gene) without a polyadenylation sequence operably linked to a splice donor sequence (SD), which is flanked by site-specific recombination sequences, e.g., FRT sequences. The gene trap element allows selection of cell clones in which integration of the vector of the invention has occurred upstream of a polyadenylation sequence. The trapped gene may be identified by any method, for example, by rapid amplification of cDNA ends (3' RACE). The sequence information derived from 3' RACE from a library of cells contacted with the vector is used to generate a database reflecting the genes that have been trapped and are represented in the cell library. To render the trapped genes functional, the gene trap element is excised in vitro by contacting the cells with the appropriate recombinase (first switch), e.g., by transfection of the cells with a vector encoding FLP recombinase (FIG. 1). The recombinase used to remove the sequences between the site-specific recombination sequences in the gene trap cassette are distinct from those used to activate the mutational element (see below) to insure production of a functional allele.

Mutational Element Cassette

The mutational element cassette comprises a mutational sequence comprising a splice acceptor sequence (SA), an internal ribosome entry site (IRES), a second marker gene (e.g., LacZ or GFP), and a polyadenylation sequence, which is flanked by a different set of site-specific recombination sites, such as mutant loxP sequences (Albert et al., 1995; Araki et al., 1997), that produce a directional bias toward inversion of the mutational sequence upon exposure to the appropriate recombinase (second switch). In one embodiment, the site-specific recombination sequences are mutant loxP sequences such as LE mutant loxP: 5' ATAACTTCG-TATA ATGTATGC TATACGAA<u>CGGTA</u> 3' (SEQ ID NO:1) and RE mutant loxP: 5' ATAACTTCGTATA GCATACAT TATACGAA<u>CGGTA</u> 3' (SEQ ID NO:2) (the mutated nucleotides are underlined). After inversion, the mutational element is spliced into the trapped gene, resulting in expression of the second marker gene and mutation of the endogenous gene.

Results

Figure 4A:
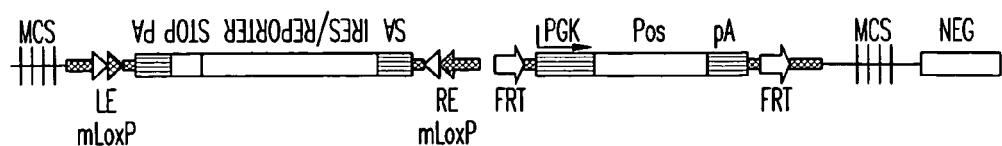
FIG. 4A is a schematic of a "flipout" vector of the invention. MCS=multi cloning site; mLoxP=mutant loxP sequences; FRT=FRT recombination sequences; IRES/Reporter=reporter gene, e.g., LacZ or GFP gene, linked to internal ribosome entry site; Pos=positive selection marker; Neg=negative selection marker; SA=splice acceptor; Stop=stop codon(s).

FIG. 4A is a schematic of a mutational cassette plasmid and restriction sites before and after inversion. An in vitro assay to detect inversion of the mutational cassette was employed. pGEM-rA DNA was incubated with Cre recombinase and samples were taken at 0, 10, 30 and 60 minutes. The products were digested with BamHI and XhoI and the digested samples separated on an agarose gel (FIG. 4B). The disappearance of a 3.6 and 2.0 kb of and the appearance of 5.0 and 0.6 kb band is indicative of inversion. FIG. 4C is a graph of densitometry results from the gel shown in FIG. 4B.

Figure 5:
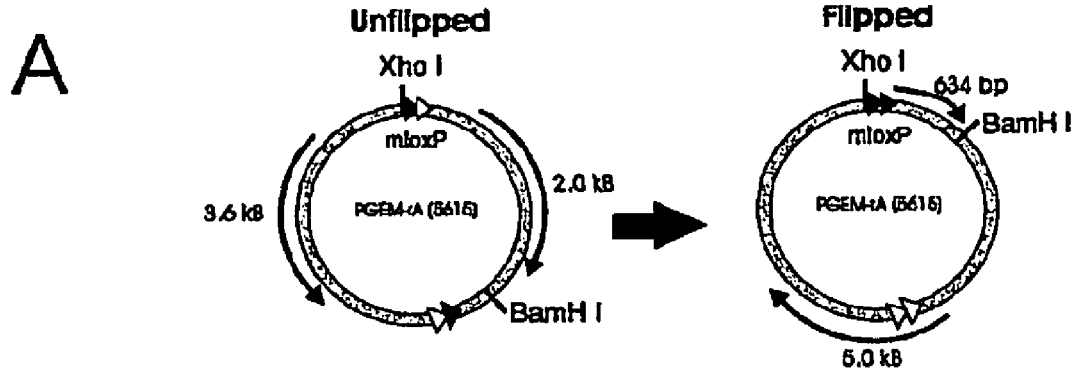
FIG. 5 shows in vitro inversion of a mutational cassette. A) A schematic of a plasmid with cassette A (mutational cassette) and restriction enzyme sites before and after inversion of the cassette. The cassette and the restriction sites (Xho I and BamH I) are shown in unflipped (left) and flipped (right) orientations. B) Agarose gel of products before and after inversion. Two µg of pGEM-rA plasmid DNA was incubated with 80 U of Cre recombinase in 80 µl Cre reaction buffer at 37° C. A 20 µl reaction mixture was aliquoted into 5 µl of 5× stop buffer (0.25% SDS, 50 mM EDTA, 2.5 mg/ml proteinase K) at 0, 10, 30, and 60 minutes, and the samples incubated at 37° C. for 20 minutes, extracted (QIAEX II), digested with BamHI and XhoI at 37° C. for 2 hours, and separated on a 0.8% agarose gel. The 5.6 kB (top) band is the linearized plasmid indicating incomplete digestion. C) Densitometry analysis of the 3.6 kB (unflipped) band from FIG. 4B normalized to 10% at time 0. There was approximately 90% inversion by one hour.
Figure 5B:
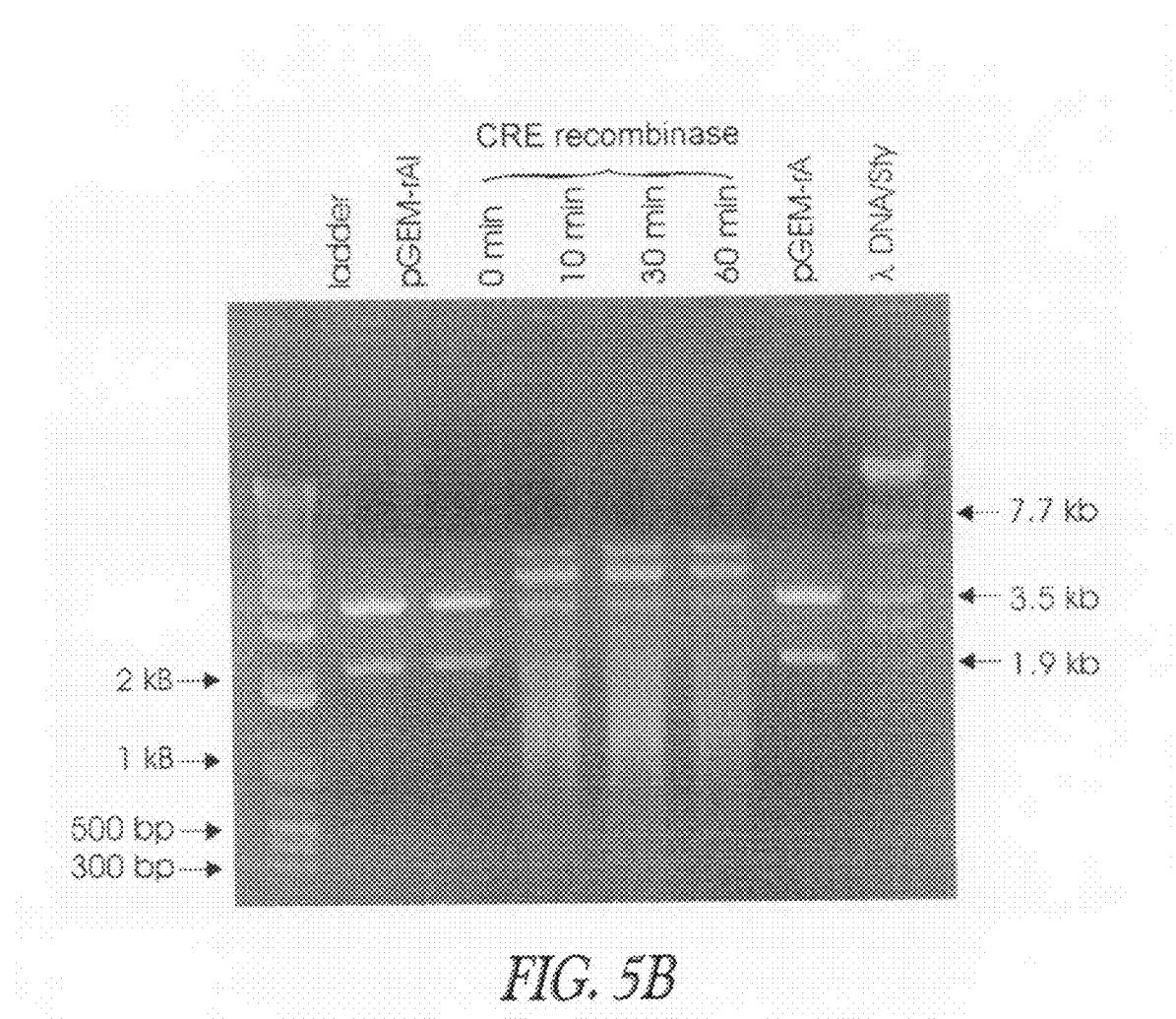
Figure 5C:
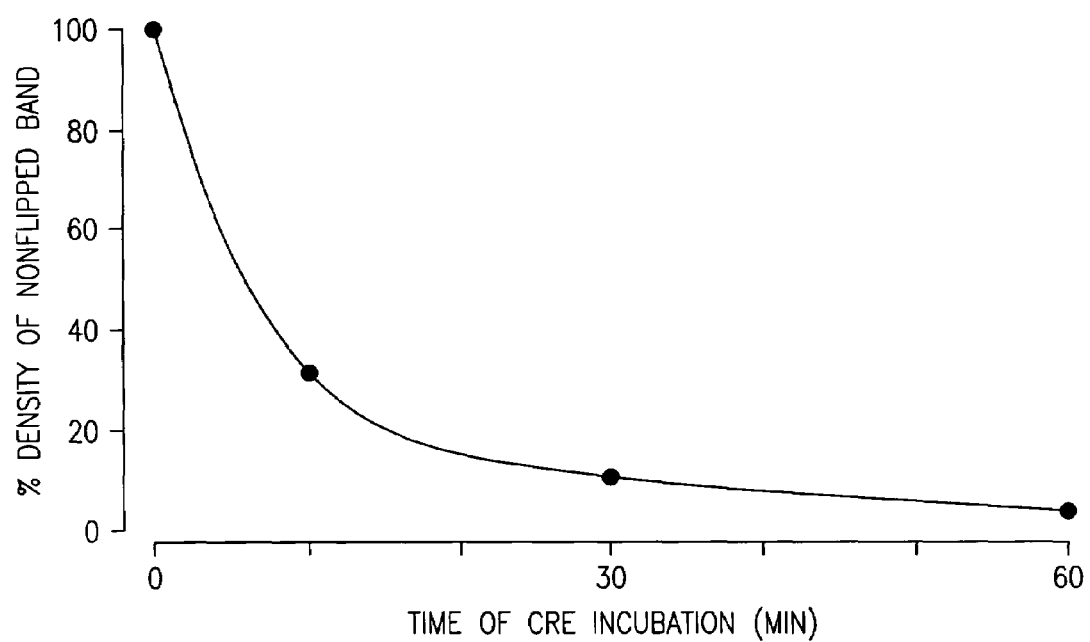
Figure 6:
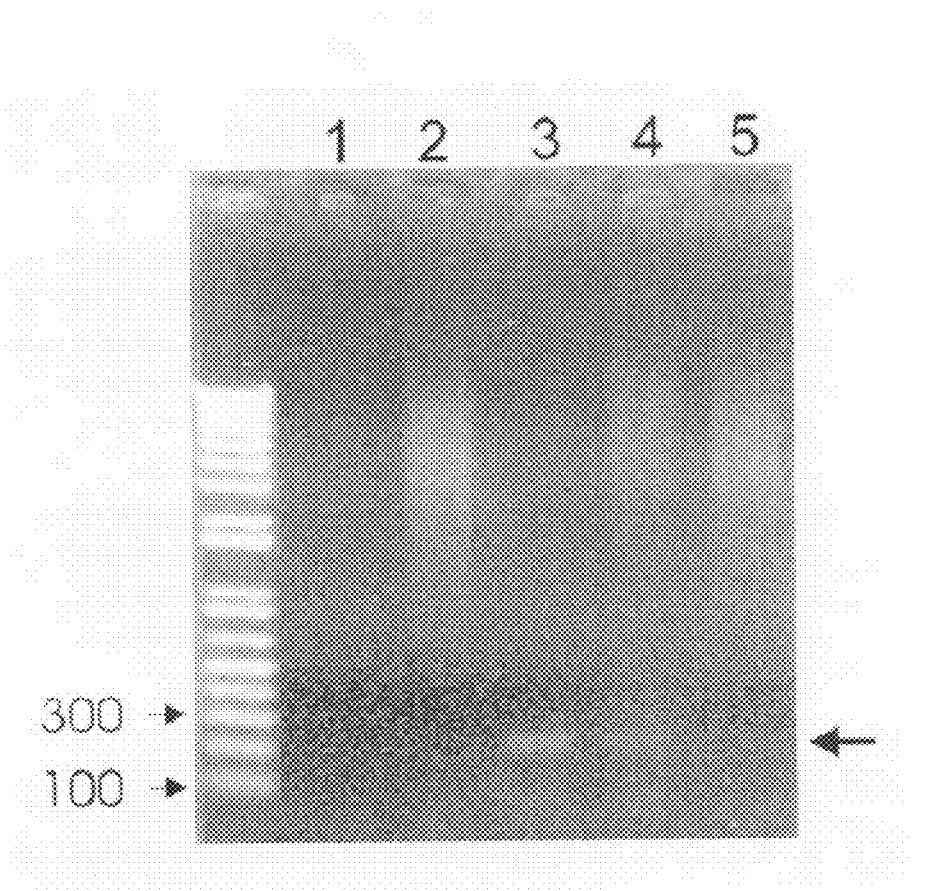
FIG. 6 illustrates inversion of a mutational cassette in R1 mouse ES cells. ES cells were electroporated with the vector and selected for 6 days in 1.5 µg/ml puromycin. Four hundred puromycin resistant clones were chosen, expanded in 96 well plates, and frozen. PCR was performed using genomic DNA prepared from individual ES cell clones as template and forward and reverse primers designed from the universal sequence in Cassette C (primer US-P1:5'CGGGATCCAG-GCAAAACGTCG3', SEQ ID NO:1, and US-P2: 5'GCTCTAGATGGTGATCCGGCC3', SEQ ID NO:2). The reaction conditions were 35 cycles at 94° C. for 30 seconds, 56° C. for 30 seconds, and 72° C. for 1 minute. PCR results indicate bands of the predicted size (232 bp) in lanes 3 and 4. Lanes shown are: 1) water control, 2) mouse genomic DNA (negative control), 3) clone A4 DNA, 4) clone A6 DNA, and 5) mouse genomic DNA.
Figure 7A:
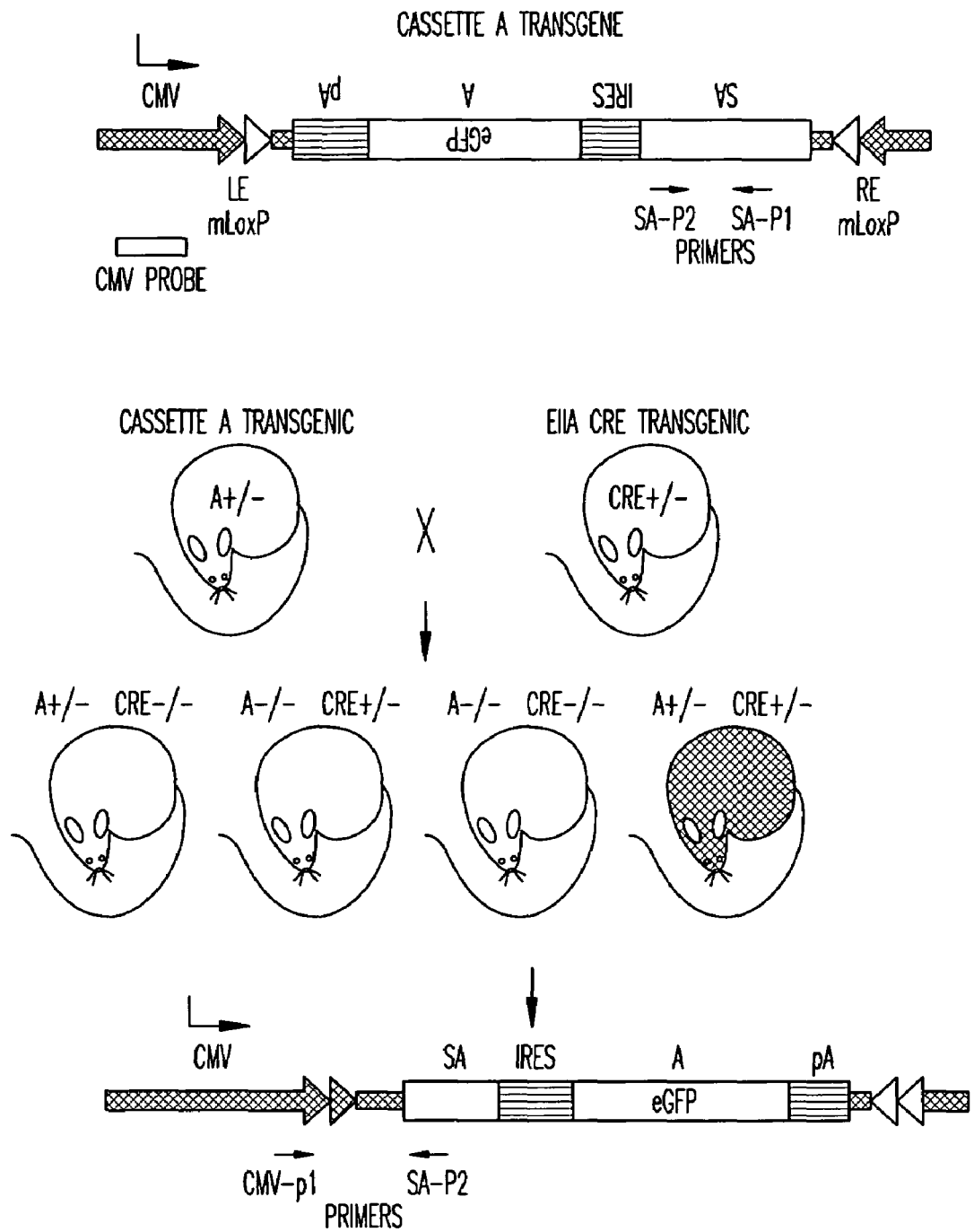
FIG. 7 shows inversion of a mutational cassette in vivo. A) Schematic of a transgene. CMV, cytomegalovirus promoter; IRES, internal ribosomal entry site; pA, polyadenylation sequence, eGFP, enhanced green fluorescent protein, RE, LE, right and left mutant LoxP sequences. Primers for Cassette A (either orientation) are SA-P1:5' AAGCTTGCTG-TATCTCTAAGA3' (SEQ ID NO:5) and SA-P2: 5'CGAAT-TCACTCACCTAGCATA3' (SEQ ID NO:6), and for inverted cassette A are CMV-P1: 5'GGTTTAGTGAACCGTCA-GATC3' (SEQ ID NO:7) and SA-P2: 5'CGAATTCACT-CACCTAGCATA3' (SEQ ID NO:8). The EIIA Cre ("deleter") mouse expresses Cre recombinase in the early mouse embryo. B) PCR analysis of 4 F1 transgenic mice (transgenic and deleter, EIIA, cross) using primers specific for Cre recombinase (left, 990 bp), Cassette A in either the original or inverted orientation (middle, 450 bp), and the inverted Cassette A (right, 550 bp). Mouse 4 is positive for the cre allele and both the original and inverted (flipped) orientations. The Cre primers are Cre P2: 5'GTTTCACTATCCAGGT-TACGG3' (SEQ ID NO:3) and Cre P1: 5'CCAATTTACT-GACCGTACACC3' (SEQ ID NO:4). C) Fluorescent image of the pancreas of mouse 4 (100×). D) Southern analysis of a second F1 line, showing both inverted (2.3 kB) and noninverted (1.0 kB) bands in a cre$^{+/-}$A$^{+/-}$ mouse. The probe is a CMV promoter probe. Because of the likely head/tail alignment of multiple transgenes, and the attendant presence of multiple LoxP sites, both bands would be expected to be observed.
Figure 7B:
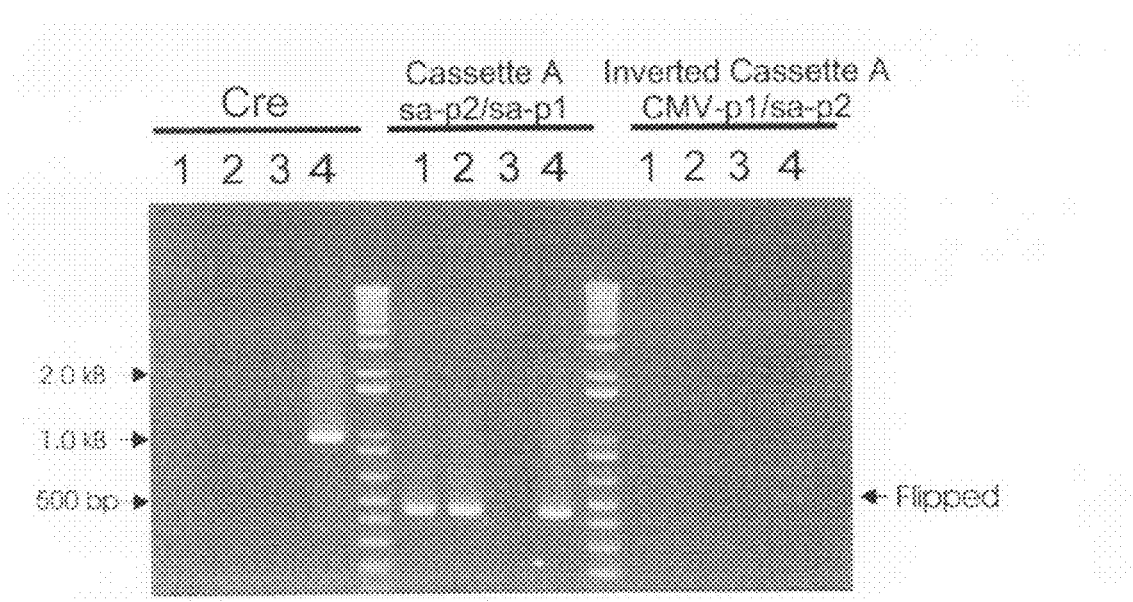
Figure 7C:
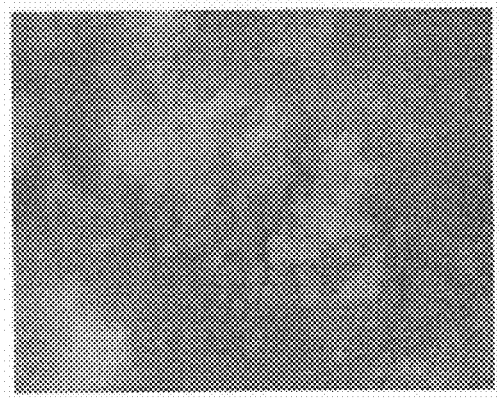
Figure 7D:
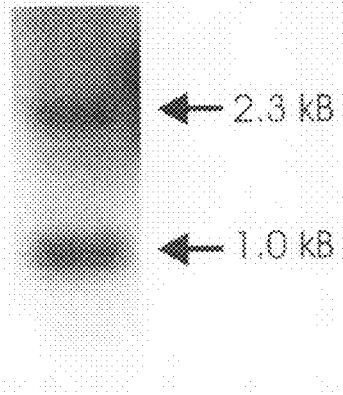

To demonstrate in vivo inversion, ES cells were electroporated with the double switch vector and transformants selected with puromycin. Four hundred puromycin-resistant clones were selected, and two of these clones were selected for this analysis. Primers were employed in an amplification reaction with genomic DNA from control mice and from the Z clones. FIG. 5 shows the in vivo inversion results.

Discussion

The double switch method and vectors allow the reactivation of the trapped gene, creating a normal allele by excising the portions of the gene trap cassette which are between the site-specific recombination sequence in vitro, i.e., the gene trap element. Prior to excision, or after excision, the trapped gene sequence can be determined. The mutational element cassette is transcriptionally silent until inversion of the mutational sequences between the second set of site-specific recombination sequences which occurs in the presence of a site-specific recombinase for those sequences. The inversion results in the inactivation of the gene in vivo in a tissue-specific or temporally controlled manner. Moreover, the marker gene in the mutational element cassette indicates the direction of the mutational sequence and thus reports whether the endogenous gene is active or inactive. In a preferred embodiment of the invention, the double switch vector sequences are incorporated into retroviral vectors, which obtain a high efficiency of single vector integrations without gross rearrangement at the site of integration.

Moreover, ES cells in which the double switch vector has been inserted can also be used to generate conventional knockout mice by inversion of the mutational element in vitro, following transfection with a vector encoding the appropriate recombinase.

EXAMPLE 2

Universal Gene Targeting Vector for Conditional Inactivation

Due to the emerging availability of complete genomic sequences, it will be possible to identify any gene and design primers to rapidly amplify any genomic DNA of interest. The method described hereinbelow allows for the use of this information to amplify flanking regions of DNA within a gene and to place these on either side of a conditionally mutational element. The method employs a plasmid comprising multiple cloning sites at two regions and an intervening mutational cassette. The homologous (targeting) segments of DNA (e.g., long arm and short arm) are inserted on either side of the mutational cassette, which is inverted relative to the reading frame of the targeting DNA. The mutational element is flanked by site-specific recombination sequences, e.g., mutant LoxP sites, in a manner that promotes an irreversible inversion of the mutational sequence upon exposure to the corresponding recombinase, e.g., Cre-recombinase. Such a targeting vector, when transformed into ES cells, results in transgenic ES clones with insertions in individual genes. Those transgenic ES cells are then available for the production of mice with conditional gene knockouts or knock-ins so called "Flipout" mice. Moreover, the transgenic ES cells are also useful to generate conventional knockout mice by inversion of the mutational element in vitro.

Breeding of homozygous mice created from ES cells in which the targeting vector has been homologously introduced (to target DNA) to mice expressing Cre-recombinase in a tissue-specific or -inducible manner results in Cre-mediated inversion of the 'silent' mutational element and an attendant disruption of the trapped gene. The availability of numerous transgenic mice expressing Cre-recombinase in a tissue-specific or temporally controlled manner, and the rapid further development of such mice (e.g., Nagy, 2000), allows "Flipout" mice to be used for the generation of targeted knockouts in virtually any tissue or organ system.

Figure 3A:
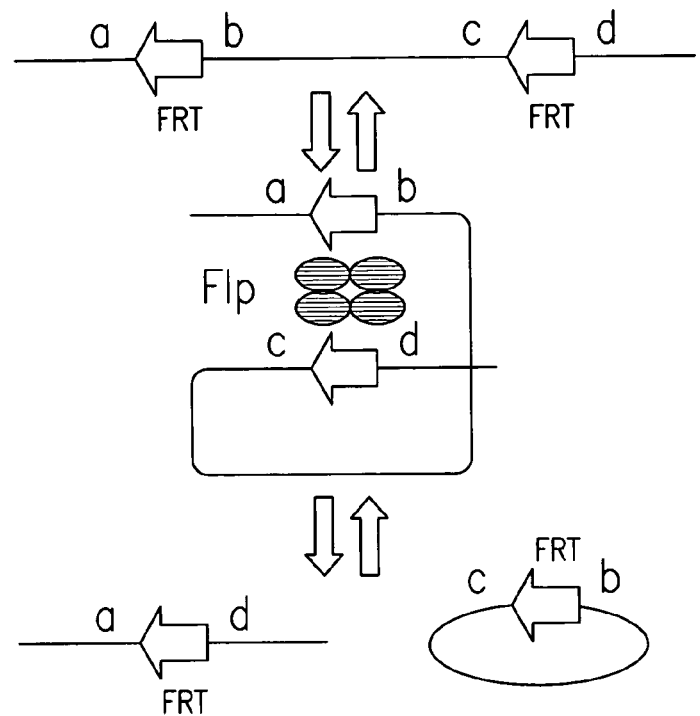
FIG. 3 illustrates Flp-recombinase-mediated excision (A) and inversion (B).
Figure 3B:
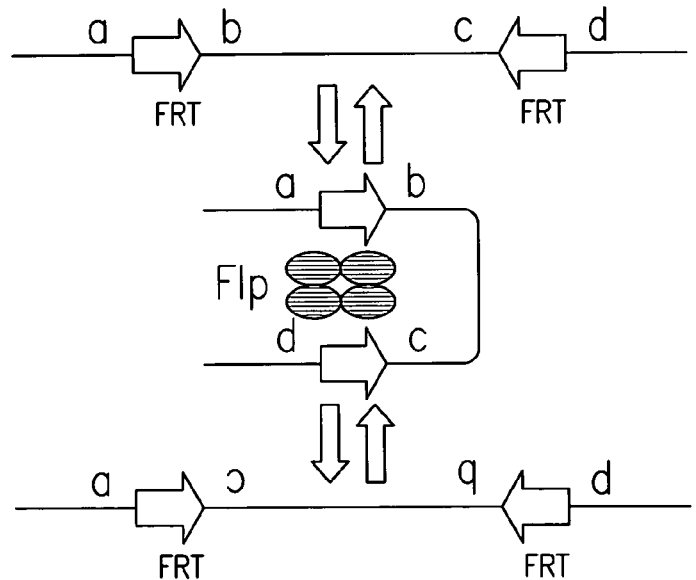

One example of a universal gene targeting vector for use with ES cells, is shown in FIG. 3A. The mutational element is initially inverted (silent) and is subsequently flipped (conditionally activated) to create a gene knock-out within the target DNA which is homologous to the targeting DNA in the vector DNA.

Mutational Element

The inverted mutational element consists of a splice acceptor sequence (SA), an internal ribosome entry sequence (IRES), and a reporter gene (eGFP) with a stop codon and polyadenylation sequence. The inverted mutational element is flanked by mutant LoxP sites in a manner that produces a directional bias toward inversion of the mutational sequence upon exposure to Cre-recombinase. Once inverted, the mutational element is spliced into the trapped gene resulting in expression of the reporter gene and premature termination of the endogenous mRNA. Albert et al. (1995) first reported that site-directed DNA integration can be achieved by using a pair of mutant loxP sites, a right element (RE) mutant loxP site and a left element (LE) mutant loxP site in ES cells (Albert et al., 1995). Later, Araki et al. (1997) found that the frequency of site-specific integration through the mutant loxP sites reached a maximum of 16% compared with the low frequency (<0.5%%) of wild type loxP sites in ES cells. Several investigators have reported Cre-induced gene inversion in vivo for purposes other than conditional mutation, using non-mutated LoxP sequences (Lam and Rajewsky, 1998; Kano et al., 1998; Kmita et al., 2000), thus confirming the essential feasibility of this approach. The mutant LoxP system produces a reaction biased toward an irreversible gene inversion. The specific mutant loxP sequences to be used are listed below and the mutated nucleotides are underlined and italicized.

LoxP Sequences

```
LE mutant loxP:
                                              (SEQ ID NO:9)
                         ———>
5' ATAACTTCGTATA ATGTATGC TATACGAA CGGTA 3'

RE mutant loxP:
                                              (SEQ ID NO:10)
                         <———
5' ATAACTTCGTATA GCATACAT TATACGAACGGTA 3'.
```

An analgous strategy may be employed for FRT sites recognized by Flp recombinase. This recombinase, derived from *Saccharomyces cerevisiae*, functions normally to invert sequences for plasmid amplification and can be used to invert the mutational cassette. The mutant FRT sequences listed below can be used to produce a reaction biased toward an irreversible inversion (Senecoff et al., 1988). The mutated nucleotides are underlined and italicized.

FRT Sequences

```
                                                                        (SEQ ID NO:11)
                                               ———>
LE mutant FRT: 5' GAAGTTCCTATTCC GAAGTTCCTATTC TCTAGAAA GTATA AGAACTTC 3'

(SEQ ID NO:12)
                                               <———
RE mutant FRT: 5' GAAGTTCCTATAC TTTCTAGA GAATA AGAACTTC GGAATAGGAACTTC 3'
```

Thus, the gene targeting vector of the invention comprises: 1) a mutational element that is transcriptionally silent, but spliced into mRNA resulting in an inactivation of the gene; 2) a reporter that indicates the transcriptional status of the mutational element; 3) a plasmid vector that incorporates multiple cloning sites for the efficient insertion of homologous (targeting) DNA sequences. The method of the invention greatly facilitates the investigation of the function of individual genes by a rapid extension of the conditional knockout approach utilizing the sequence information from the human and mouse genomes. The benefits of this approach include the potential to discover novel phenotypes and create useful in vivo model systems for the study of disease. The strategy is particularly well suited for studying embryonic development. Moreover, because the inactivation of many genes will be lethal or result in developmental adaptations, it is very useful to have the capability to inactivate or "knockout" a gene in an animal in a temporally or spatially controlled (conditional) manner. Thus, the invention provides a method for random insertional and conditional mutagenesis of genes.

REFERENCES

Abremaid et al., *Cell,* 32: 1301 (1983).
Albert et al., *Plant J.,* 7:649 (1995).
Araki et al., *Nucleic Acids Res.,* 25:868 (1997).
Araki et al., *J. Mol. Biol.,* 225: 25 (1992).
Ausubel et al. (eds) Current Protocols in Molecular Biology, John Wiley & Sons (1989).
Caplitt and Loewy, eds., Viral Vectors: Gene Therapy and Neuroscience Applications, Academic Press, San Diego (1995).
Casadaban and Cohen, *PNAS,* 76:4530 (1980).
Chu and Sharp, *Nature,* 289:378 (1981).
Enomoto et al., *J. Bacteriol.,* 156: 663 (1983).
Friedrich and Soriano, *Genes & Devel.,* 5:1513 (1991).
Frohman, *PCR Methods and Applications,* 4:S40 (1994).
Golic and Lindquist, *Cell,* 59: 499(1989).
Gossler et al., *Science,* 244 (1989).
Hoess et al., *Proc. Natl. Acad. Sci. USA,* 79: 3398 (1982).
Ito et al., *Nuc. Acid Res.,* 10:1755 (1982).
Kano et al., *BBRC,* 248: 806 (1998).
Kmita et al., *Nature Genetics,* 26: 452 (2000).
Lam and Rajewsky, *Proc. Natl. Acad. Sci. USA,* 95: 13171 (1998).
Lyon et al., eds. "Genetic Variants and Strains of the Laboratory Mouse" 3rd Ed., Vols. 1 and 2, 1996, Oxford University Press, NY, N.Y (1996).
Maeser et al., *Mol. Gen. Genetics,* 230: 170 (1991).
Nagy, *Genesis,* 26:99 (2000)
Ogilvie et al., *Science,* 214: 270 (1981).
Sambrook et al., Molecular Cloning Vols. I-III, Cold Spring Harbor Laboratory Press, Cold Spring Harbor, N.Y. (1989).
Senecoff et al., *J. Mol. Biol.* 201: 405 (1988).
Weber et al., *Cell,* 36:983-992 (1984).
Wiles et al., *Nat Genet.,* 24:13 (2000).
Zambrowicz et al. *Nature.,* 392:608 (1998).

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

---

What is claimed is:

1. A genetically engineered vector comprising:
   a) a mutational element cassette comprising operably linked:
      i) a DNA comprising a first site-specific recombination sequence for a first recombinase;
      ii) a DNA comprising a mutational sequence which comprises a splice acceptor sequence linked to a first marker gene linked to a polyadenylation sequence; and
      iii) a DNA comprising a second site-specific recombination sequence for the first recombinase, wherein the first and second site-specific recombination sequences in a)i and a)iii are mutant sequences that are substrates for the first recombinase; and
   b) a gene trap cassette comprising operably linked:
      i) a DNA comprising a first site-specific recombination sequence for a second recombinase;
      ii) a DNA comprising a first gene trap element comprising a promoter operably linked to a second marker gene operably linked to a splice donor sequence and a second gene trap cassette comprising promoter operably linked to a unique sequence not present in the genome of a selected host cell; and
      iii) a DNA comprising a second site-specific recombination sequence for the second recombinase;
   wherein the gene trap cassette is 3' to the mutational element cassette, wherein the first and second recombinases are different, wherein the DNA of a)i and the DNA of a)iii) are in opposite orientation to each other, and wherein the DNA of b)i) and the DNA of b)iii) are in the same orientation, wherein if the vector inserts into an exon in the genome of the cell and is expressed, the unique sequence is present in a RNA transcript but if the vector inserts into an intron in the genome of the cell and is expressed, the unique sequence is not spliced into mRNA.

2. The vector of claim 1 wherein DNA comprising the mutational sequence is inverted relative to the DNA of b)ii).

3. The vector of claim 1 wherein the second marker gene is a selectable marker gene.

4. The vector of claim 1 wherein the DNA of a)i) and the DNA of a)iii) are lox sequences.

5. The vector of claim 1 wherein the DNA of b)i) and the DNA of b)iii) are flip recombinase recognition sequences (FRT) sequences.

6. The vector of claim 5 further comprising a 5' LTR and a 3' LTR and a third site-specific recombination sequence for the second recombinase, wherein the 3' LTR is 5' to the mutational element cassette and the 5' LTR is 3' to the gene trap cassette, wherein the third site-specific recombination sequence is 3' to the 3' LTR and 5' to the DNA of a)i) and is in an orientation that is inverted relative to the DNA of b)i) and b)iii), wherein the DNA of a)ii) is in the same orientation as the DNA of b)ii), and wherein the LTRs are positioned so that transcription from the 5' LTR is in the opposite orientation as transcription from the promoters in the DNA of b)ii).

7. The vector of claim 1 wherein the mutational sequence further comprises an internal ribosome entry site operatively positioned between the splice acceptor sequence and the initiation codon of the second marker gene.

8. The vector of claim 1 wherein the first or the second marker gene is selected from the group consisting of a marker conferring antibiotic resistance, an enzymatic marker, and a fluorescently detectable marker.

9. The vector of claim 8 wherein the first marker gene is green fluorescent protein (Gfp) or LacZ.

10. The vector of claim 8 wherein the second marker gene encodes neomycin or puromycin resistance.

11. The vector of claim 1 further comprising a DNA sequence which is 5' to the mutational element cassette and comprises a multiple cloning site.

12. The vector of claim 1 wherein the DNA of a)i) and the DNA of a)iii) are mutant lox sequences and the DNA of b)i) and the DNA of b)iii) are FRT sequences.

13. A method of gene trapping comprising:
   a) introducing a vector into a mammalian cell in vitro to yield genetically altered mammalian cells, wherein the vector comprises:
      i) a mutational element cassette comprising operably linked: a DNA comprising a first site-specific recombination sequence for a first recombinase; a DNA comprising a mutational sequence which comprises a splice acceptor sequence linked to a first marker gene linked to a polyadenylation sequence; and a DNA comprising a second site-specific recombination sequence for the first recombinase, wherein the first and second site-specific recombination sequences in a)i and a)iii are mutant sequences that are substrates for the first recombinase; and ii) a gene trap cassette comprising operably linked: a DNA comprising a first site-specific recombination sequence for a second recombinase; a DNA comprising a first gene trap element comprising a promoter operably linked to a second marker gene operably linked to a splice donor sequence and a second gene trap cassette comprising promoter operably linked to a unique sequence;

and a DNA comprising a second site-specific recombination sequence for the second recombinase;

wherein the gene trap cassette is 3' to the mutational element cassette, wherein the first and second recombinases are different, wherein the DNA comprising the first site-specific recombination sequence for the first recombinase and the DNA comprising the second site-specific recombination sequence for the first recombinase are in opposite orientation to each other, and wherein the DNA comprising the first site-specific recombination sequence for the second recombinase, and the DNA comprising the second site-specific recombination sequence for the second recombinase are in the same orientation, wherein if the vector inserts into an exon in the genome of the cell and is expressed, the unique sequence is present in a RNA transcript but if the vector inserts into an intron in the genome of the cell and is expressed, the unique sequence is not spliced into mRNA; and b) identifying at least one first genetically altered cell, the genome of which comprises the vector and expresses the second marker gene.

14. The method of claim 13 wherein the introduction of the vector to the cell is via electroporation, viral infection, retrotransposition, microinjection, or transfection.

15. The method of claim 13 further comprising isolating the first genetically altered cell.

16. The method of claim 13 wherein the mammalian cell is a murine, rat or human cell.

17. The method of claim 13 wherein the first genetically altered cell is a rodent embryonic stem cell.

18. The method of claim 13 further comprising c) introducing to the first genetically altered cell the second recombinase to yield a second genetically altered cell, the genome of which has undergone a recombination event relative to the first genetically altered cell such that the genome of the second genetically altered cell does not comprise the gene trap element and one of the site-specific recombination sequences for the second recombinase.

19. An isolated second genetically altered cell prepared by the method of claim 18.

20. The isolated second genetically altered cell of claim 19 which is a rodent embryonic stem cell.

21. The method of claim 13 wherein the DNA of a)i) and the DNA of a)iii) are mutant lox sequences and the DNA of b)i) and the DNA of b)iii) are FRT sequences.

22. The method of claim 13 wherein the mutational cassette of a) is inverted relative to the gene trap cassette of b).

* * * * *

UNITED STATES PATENT AND TRADEMARK OFFICE
CERTIFICATE OF CORRECTION

PATENT NO. : 7,449,179 B2 Page 1 of 1
APPLICATION NO. : 10/416995
DATED : November 11, 2008
INVENTOR(S) : Xin et al.

It is certified that error appears in the above-identified patent and that said Letters Patent is hereby corrected as shown below:

On the Title page, in Item (56), under "Other Publications", in column 2, line 3, delete "Moplecular" and insert -- Molecular --, therefor.

On the Title page, in Item (56), under "Other Publications", in column 2, line 21, delete "leadint" and insert -- leading --, therefor.

In column 27, line 14, in Claim 13, delete "casseffe" and insert -- cassette --, therefor.

Signed and Sealed this

Tenth Day of March, 2009

JOHN DOLL
*Acting Director of the United States Patent and Trademark Office*